US012102782B2

(12) United States Patent
Nair et al.

(10) Patent No.: US 12,102,782 B2
(45) Date of Patent: Oct. 1, 2024

(54) THROMBECTOMY AND ASPIRATION SYSTEM AND METHODS OF USE

(71) Applicant: Contego Medical, Inc., Raleigh, NC (US)

(72) Inventors: Ajit Nair, Pleasanton, CA (US); Ravish Sachar, Raleigh, NC (US); Hung Ha, Raleigh, NC (US)

(73) Assignee: Contego Medical, Inc., Raleigh, NC (US)

( * ) Notice: Subject to any disclaimer, the term of this patent is extended or adjusted under 35 U.S.C. 154(b) by 0 days.

(21) Appl. No.: 18/102,127

(22) Filed: Jan. 27, 2023

(65) Prior Publication Data
US 2023/0233818 A1   Jul. 27, 2023

Related U.S. Application Data

(60) Provisional application No. 63/303,710, filed on Jan. 27, 2022.

(51) Int. Cl.
*A61B 17/221* (2006.01)
*A61M 25/00* (2006.01)
(Continued)

(52) U.S. Cl.
CPC ......... *A61M 25/104* (2013.01); *A61B 17/221* (2013.01); *A61B 2017/00367* (2013.01);
(Continued)

(58) Field of Classification Search
CPC .... A61M 1/84; A61M 1/87; A61M 2025/109; A61M 25/104; A61B 17/221;
(Continued)

(56) References Cited

U.S. PATENT DOCUMENTS 5,882,329 A   3/1999  Patterson et al.
5,902,263 A   5/1999  Patterson et al.
(Continued)

FOREIGN PATENT DOCUMENTS

CN   113907837 A   1/2022
JP   2008167958 A   7/2008
(Continued)

OTHER PUBLICATIONS

International Search Report and Written Opinion of the International Searching Authority, issued in PCT/US2023/061431, May 30, 2023.

*Primary Examiner* — Katherine M Rodjom
(74) *Attorney, Agent, or Firm* — Meunier Carlin & Curfman LLC

(57) ABSTRACT

Devices, systems, and methods for performing thrombectomy procedures are disclosed herein. The devices can include an aspiration catheter which optionally has a beveled distal end. The aspiration catheter is advanced to a position adjacent a thrombus. A blocking element can be expanded near the distal end of the aspiration catheter to block fluid flow during the procedure. The devices can include a thrombus retrieval device supporting a braided assembly that grips and facilitates removal of the thrombus. The braided assembly is expandable to a range of expanded outer diameters by varying the level of tension in an activation wire attached thereto. An expander can be deployed beneath the braided assembly to exert an outward expansion force upon the braid, thereby increasing the grip between the braided assembly and the thrombus. The braided assembly contacts the thrombus and the retrieval device pulls it proximally toward the aspiration catheter.

20 Claims, 20 Drawing Sheets

(51) Int. Cl.
*A61M 25/10* (2013.01)
*A61B 17/00* (2006.01)

(52) U.S. Cl.
CPC .............. *A61M 2025/1088* (2013.01); *A61M 2025/109* (2013.01)

(58) Field of Classification Search
CPC .. A61B 2017/2212; A61B 2017/22034; A61B 2017/22038; A61B 2017/22039; A61B 2017/22079; A61B 17/1214; A61B 17/12145; A61B 17/1215; A61B 17/12154; A61B 17/1268; A61B 17/12177
See application file for complete search history.

(56) References Cited

U.S. PATENT DOCUMENTS

| | | | |
|---|---|---|---|
| 5,941,869 A | 8/1999 | Patterson et al. | |
| 5,972,019 A * | 10/1999 | Engelson | A61B 17/3207 606/159 |
| 6,066,149 A | 5/2000 | Samson et al. | |
| 6,066,158 A | 5/2000 | Engelson | |
| 6,146,396 A | 11/2000 | Konya et al. | |
| 6,319,242 B1 | 11/2001 | Patterson et al. | |
| 6,454,741 B1 | 9/2002 | Muni et al. | |
| 7,063,714 B2 | 6/2006 | Dorros et al. | |
| 7,169,161 B2 | 1/2007 | Bonnette et al. | |
| 7,220,269 B1 | 5/2007 | Ansel et al. | |
| 7,625,337 B2 | 12/2009 | Campbell et al. | |
| 7,645,290 B2 | 1/2010 | Lucas | |
| 7,766,934 B2 | 8/2010 | Pal et al. | |
| 7,914,549 B2 | 3/2011 | Morsi | |
| 7,931,659 B2 | 4/2011 | Bose et al. | |
| 8,043,313 B2 | 10/2011 | Krolik et al. | |
| RE43,882 E | 12/2012 | Hopkins et al. | |
| 8,366,735 B2 | 2/2013 | Bose et al. | |
| 8,425,549 B2 | 4/2013 | Lenker et al. | |
| 8,444,661 B2 | 5/2013 | Nair et al. | |
| 8,460,312 B2 | 6/2013 | Bose et al. | |
| 8,460,313 B2 | 6/2013 | Huffmaster | |
| 8,758,325 B2 | 6/2014 | Webster et al. | |
| 8,758,364 B2 | 6/2014 | Eckhouse et al. | |
| 8,784,434 B2 | 7/2014 | Rosenbluth et al. | |
| 8,864,792 B2 | 10/2014 | Eckhouse et al. | |
| 8,926,649 B2 | 1/2015 | Krolik et al. | |
| 8,939,991 B2 | 1/2015 | Krolik et al. | |
| 8,945,160 B2 | 2/2015 | Krolik et al. | |
| 9,005,237 B2 | 4/2015 | Eckhouse et al. | |
| 9,017,309 B2 | 4/2015 | Tanikawa et al. | |
| 9,034,008 B2 | 5/2015 | Eckhouse et al. | |
| 9,078,682 B2 | 7/2015 | Lenker et al. | |
| 9,101,382 B2 | 8/2015 | Krolik et al. | |
| 9,119,656 B2 | 9/2015 | Bose et al. | |
| 9,149,609 B2 | 10/2015 | Ansel et al. | |
| 9,259,237 B2 | 2/2016 | Quick et al. | |
| 9,408,620 B2 | 8/2016 | Rosenbluth et al. | |
| 9,510,930 B2 | 12/2016 | Patel et al. | |
| 9,526,865 B2 | 12/2016 | Quick | |
| 9,533,124 B2 | 1/2017 | Mack et al. | |
| 9,579,116 B1 | 2/2017 | Nguyen et al. | |
| 9,597,101 B2 | 3/2017 | Galdonik et al. | |
| 9,636,206 B2 | 5/2017 | Nguyen et al. | |
| 9,655,633 B2 | 5/2017 | Leynov et al. | |
| 9,700,332 B2 | 7/2017 | Marchand et al. | |
| 9,731,099 B2 | 8/2017 | Krolik et al. | |
| 9,744,024 B2 | 8/2017 | Nguyen et al. | |
| 9,750,517 B2 | 9/2017 | Agrawal | |
| 9,757,137 B2 | 9/2017 | Krolik et al. | |
| 9,801,643 B2 | 10/2017 | Hansen et al. | |
| 9,814,477 B2 | 11/2017 | Jensen | |
| 9,827,084 B2 | 11/2017 | Bonnette et al. | |
| 9,833,599 B2 | 12/2017 | Krolik et al. | |
| 9,839,771 B2 | 12/2017 | Eversull et al. | |
| 9,844,386 B2 | 12/2017 | Nguyen et al. | |
| 9,844,387 B2 | 12/2017 | Marchand et al. | |
| 9,855,067 B2 | 1/2018 | Krolik et al. | |
| 9,883,877 B2 | 2/2018 | Look et al. | |
| 9,943,321 B2 | 4/2018 | Nita | |
| 9,943,323 B2 | 4/2018 | Martin et al. | |
| 9,999,493 B2 | 6/2018 | Nguyen et al. | |
| 10,004,531 B2 | 6/2018 | Rosenbluth et al. | |
| 10,130,387 B2 | 11/2018 | McRae et al. | |
| 10,149,692 B2 | 12/2018 | Turjman et al. | |
| 10,271,864 B2 | 4/2019 | Greenhalgh et al. | |
| 10,300,256 B2 | 5/2019 | Aboytes | |
| 10,314,608 B2 | 6/2019 | Jenson et al. | |
| 10,335,260 B2 | 7/2019 | Janardhan et al. | |
| 10,383,644 B2 | 8/2019 | Molaei et al. | |
| 10,383,751 B2 | 8/2019 | Ferrera et al. | |
| 10,420,570 B2 | 9/2019 | Vale et al. | |
| 10,485,551 B2 | 11/2019 | Turjman et al. | |
| 10,499,944 B2 | 12/2019 | Mallaby | |
| 10,555,752 B2 | 2/2020 | Robertson et al. | |
| 10,617,435 B2 | 4/2020 | Vale et al. | |
| 10,624,659 B2 | 4/2020 | Gamba et al. | |
| 10,660,737 B2 | 5/2020 | Von Lehe et al. | |
| 10,682,152 B2 | 6/2020 | Vale et al. | |
| 10,687,834 B2 | 6/2020 | Follmer et al. | |
| 10,702,367 B2 | 7/2020 | Sachar et al. | |
| 10,716,915 B2 | 7/2020 | Ogle et al. | |
| 10,751,159 B2 | 8/2020 | Janardhan et al. | |
| 10,842,498 B2 | 11/2020 | Vale et al. | |
| 10,898,215 B2 | 1/2021 | Horowitz | |
| 10,952,757 B2 | 3/2021 | Galdonik et al. | |
| 11,020,212 B2 | 6/2021 | Friedman | |
| 11,027,093 B2 | 6/2021 | Haldis et al. | |
| 11,051,928 B2 | 7/2021 | Casey et al. | |
| 11,065,017 B2 | 7/2021 | Spence | |
| 11,065,020 B2 | 7/2021 | Chida et al. | |
| 11,090,466 B1 | 8/2021 | Nicholson | |
| 11,096,712 B2 | 8/2021 | Teigen et al. | |
| 11,103,627 B2 | 8/2021 | Garrison et al. | |
| 11,154,314 B2 | 10/2021 | Quick | |
| 11,166,802 B2 | 11/2021 | Sachar et al. | |
| 11,197,977 B2 | 12/2021 | Mullins et al. | |
| 11,224,449 B2 | 1/2022 | Chou et al. | |
| 11,259,824 B2 | 3/2022 | Brady et al. | |
| 11,272,945 B2 | 3/2022 | Shrivastava et al. | |
| 11,305,094 B2 | 4/2022 | Garrison et al. | |
| 11,318,282 B2 | 5/2022 | Garrison et al. | |
| 11,376,027 B2 | 7/2022 | Martin et al. | |
| 11,376,028 B1 | 7/2022 | Saadat et al. | |
| 11,395,665 B2 | 7/2022 | Yang et al. | |
| 11,395,667 B2 | 7/2022 | Vale et al. | |
| 11,399,711 B2 | 8/2022 | Cooper et al. | |
| 11,406,405 B2 | 8/2022 | Molaei | |
| 11,413,054 B2 | 8/2022 | Ulm | |
| 11,432,835 B2 | 9/2022 | Shaffer et al. | |
| 11,471,582 B2 | 10/2022 | Yee | |
| 11,490,908 B2 | 11/2022 | Sachar et al. | |
| 11,490,910 B2 | 11/2022 | Leuthardt et al. | |
| 11,504,151 B2 | 11/2022 | Deaton et al. | |
| 2002/0016624 A1 | 2/2002 | Patterson et al. | |
| 2006/0058837 A1 | 3/2006 | Bose et al. | |
| 2007/0016041 A1 | 1/2007 | Nita | |
| 2007/0293887 A1 | 12/2007 | Okushi et al. | |
| 2008/0167678 A1 | 7/2008 | Morsi | |
| 2008/0249420 A1 * | 10/2008 | Crossman | A61M 25/1002 604/523 |
| 2008/0306499 A1 | 12/2008 | Katoh et al. | |
| 2010/0036312 A1 * | 2/2010 | Krolik | A61M 25/0068 606/159 |
| 2010/0036410 A1 | 2/2010 | Krolik et al. | |
| 2010/0114017 A1 | 5/2010 | Lenker et al. | |
| 2010/0204672 A1 | 8/2010 | Lockhart et al. | |
| 2011/0125132 A1 | 5/2011 | Krolik et al. | |
| 2011/0152920 A1 | 6/2011 | Eckhouse et al. | |
| 2011/0160621 A1 | 6/2011 | Nita | |
| 2011/0202088 A1 | 8/2011 | Eckhouse et al. | |
| 2011/0319927 A1 | 12/2011 | Nita | |
| 2012/0078096 A1 | 3/2012 | Krolik et al. | |
| 2012/0078140 A1 | 3/2012 | Nita | |
| 2012/0101510 A1 | 4/2012 | Lenker et al. | |

(56) References Cited

U.S. PATENT DOCUMENTS

| | | |
|---|---|---|
| 2012/0109057 A1 | 5/2012 | Krolik et al. |
| 2012/0150147 A1 | 6/2012 | Leynov et al. |
| 2012/0197193 A1 | 8/2012 | Krolik et al. |
| 2012/0265283 A1 | 10/2012 | Mack et al. |
| 2012/0330196 A1 | 12/2012 | Nita |
| 2013/0325055 A1 | 12/2013 | Eckhouse et al. |
| 2013/0325056 A1 | 12/2013 | Eckhouse et al. |
| 2014/0188127 A1 | 7/2014 | Dubrul et al. |
| 2014/0188156 A1 | 7/2014 | Tekulve et al. |
| 2014/0214067 A1 | 7/2014 | Sachar et al. |
| 2014/0236219 A1 | 8/2014 | Dubrul et al. |
| 2014/0243885 A1 | 8/2014 | Eckhouse et al. |
| 2014/0303554 A1 | 10/2014 | Krolik et al. |
| 2014/0324091 A1 | 10/2014 | Rosenbluth et al. |
| 2014/0343663 A1 | 11/2014 | Sudin et al. |
| 2015/0119896 A1 | 4/2015 | Krolik et al. |
| 2015/0190221 A1 | 7/2015 | Schaefer et al. |
| 2015/0202416 A1 | 7/2015 | Krolik et al. |
| 2015/0238207 A1 | 8/2015 | Cox et al. |
| 2015/0320983 A1 | 11/2015 | Krolik et al. |
| 2015/0352325 A1 | 12/2015 | Quick |
| 2015/0359549 A1 | 12/2015 | Lenker et al. |
| 2016/0038174 A1* | 2/2016 | Bruzzi ............ A61B 17/320758 606/159 |
| 2016/0143721 A1 | 5/2016 | Rosenbluth et al. |
| 2016/0166265 A1 | 6/2016 | Nita |
| 2016/0220346 A1 | 8/2016 | Bonnette et al. |
| 2016/0262790 A1 | 9/2016 | Rosenbluth et al. |
| 2016/0287276 A1 | 10/2016 | Cox et al. |
| 2017/0035445 A1 | 2/2017 | Nguyen et al. |
| 2017/0079672 A1 | 3/2017 | Quick |
| 2017/0086960 A1 | 3/2017 | Nguyen et al. |
| 2017/0105745 A1 | 4/2017 | Rosenbluth et al. |
| 2017/0112514 A1 | 4/2017 | Marchand et al. |
| 2017/0119408 A1 | 5/2017 | Ma |
| 2017/0119409 A1 | 5/2017 | Ma |
| 2017/0119974 A1* | 5/2017 | Racz .................. A61M 5/32 |
| 2017/0143359 A1 | 5/2017 | Nguyen et al. |
| 2017/0189041 A1 | 7/2017 | Cox et al. |
| 2017/0215902 A1 | 8/2017 | Leynov et al. |
| 2017/0216503 A1 | 8/2017 | Look et al. |
| 2017/0224366 A1 | 8/2017 | Nguyen et al. |
| 2017/0259042 A1 | 9/2017 | Nguyen et al. |
| 2017/0290598 A1 | 10/2017 | Culbert et al. |
| 2017/0325839 A1 | 11/2017 | Rosenbluth et al. |
| 2017/0325931 A1 | 11/2017 | Bonnette et al. |
| 2017/0333076 A1 | 11/2017 | Bruzzi et al. |
| 2017/0367720 A1 | 12/2017 | Krolik et al. |
| 2018/0028209 A1 | 2/2018 | Sudin et al. |
| 2018/0055619 A1 | 3/2018 | Nguyen et al. |
| 2018/0092652 A1 | 4/2018 | Marchand et al. |
| 2018/0092653 A1 | 4/2018 | Krolik et al. |
| 2018/0093080 A1 | 4/2018 | Krolik et al. |
| 2018/0103969 A1 | 4/2018 | Ma |
| 2018/0125512 A1 | 5/2018 | Nguyen et al. |
| 2018/0193043 A1 | 7/2018 | Marchand et al. |
| 2018/0206862 A1 | 7/2018 | Long |
| 2018/0338770 A1* | 11/2018 | Mogi .................. A61M 25/007 |
| 2018/0368965 A1* | 12/2018 | Janardhan ............. A61B 90/39 |
| 2019/0133616 A1* | 5/2019 | Sachar .................. A61B 17/22 |
| 2020/0029983 A1 | 1/2020 | Lattouf |
| 2020/0029998 A1 | 1/2020 | Ogle et al. |
| 2020/0046368 A1 | 2/2020 | Merritt et al. |
| 2020/0205845 A1* | 7/2020 | Yang ................ A61M 25/0108 |
| 2020/0246036 A1 | 8/2020 | Kallmes et al. |
| 2020/0337716 A1 | 10/2020 | Garrison et al. |
| 2020/0353205 A1 | 11/2020 | Kelly et al. |
| 2020/0375616 A1 | 12/2020 | Fitz et al. |
| 2020/0405336 A1 | 12/2020 | Martin et al. |
| 2021/0085931 A1 | 3/2021 | Green et al. |
| 2021/0128185 A1 | 5/2021 | Nguyen et al. |
| 2021/0153884 A1 | 5/2021 | Casey et al. |
| 2021/0154443 A1 | 5/2021 | Casey et al. |
| 2021/0169509 A1 | 6/2021 | Goyal |
| 2021/0236778 A1 | 8/2021 | Kim et al. |
| 2021/0275198 A1 | 9/2021 | Keating et al. |
| 2021/0298773 A1 | 9/2021 | Echarri et al. |
| 2021/0298775 A1 | 9/2021 | Nguyen et al. |
| 2021/0308431 A1 | 10/2021 | Jalgaonkar et al. |
| 2021/0393275 A1 | 12/2021 | Whelan |
| 2021/0393277 A1 | 12/2021 | Vale et al. |
| 2022/0061863 A1 | 3/2022 | Lorenzo et al. |
| 2022/0111177 A1 | 4/2022 | Chou et al. |
| 2022/0111183 A1 | 4/2022 | Gray |
| 2022/0117614 A1 | 4/2022 | Salmon et al. |
| 2022/0125450 A1 | 4/2022 | Sirhan et al. |
| 2022/0142765 A1 | 5/2022 | Sachar et al. |
| 2022/0151647 A1 | 5/2022 | Dolendo et al. |
| 2022/0152355 A1 | 5/2022 | Dolendo et al. |
| 2022/0233204 A1 | 7/2022 | Gorochow et al. |
| 2022/0249121 A1 | 8/2022 | Wang et al. |
| 2022/0273322 A1 | 9/2022 | Goyal |
| 2022/0280175 A1 | 9/2022 | Tran et al. |
| 2022/0296262 A1 | 9/2022 | O'Malley et al. |
| 2022/0313953 A1 | 10/2022 | Goyal |
| 2022/0323087 A1 | 10/2022 | Konstantino et al. |
| 2022/0338889 A1 | 10/2022 | Sirhan et al. |

FOREIGN PATENT DOCUMENTS

| | | |
|---|---|---|
| WO | 2016071524 A1 | 5/2016 |
| WO | 2019/094749 | 5/2019 |
| WO | 2021/150227 | 7/2021 |
| WO | 2022/016096 | 1/2022 |
| WO | 2022/020366 | 1/2022 |
| WO | 2022/022458 | 2/2022 |
| WO | 2022/040615 | 2/2022 |
| WO | 2022/074423 | 4/2022 |
| WO | 2022/231966 | 11/2022 |

* cited by examiner

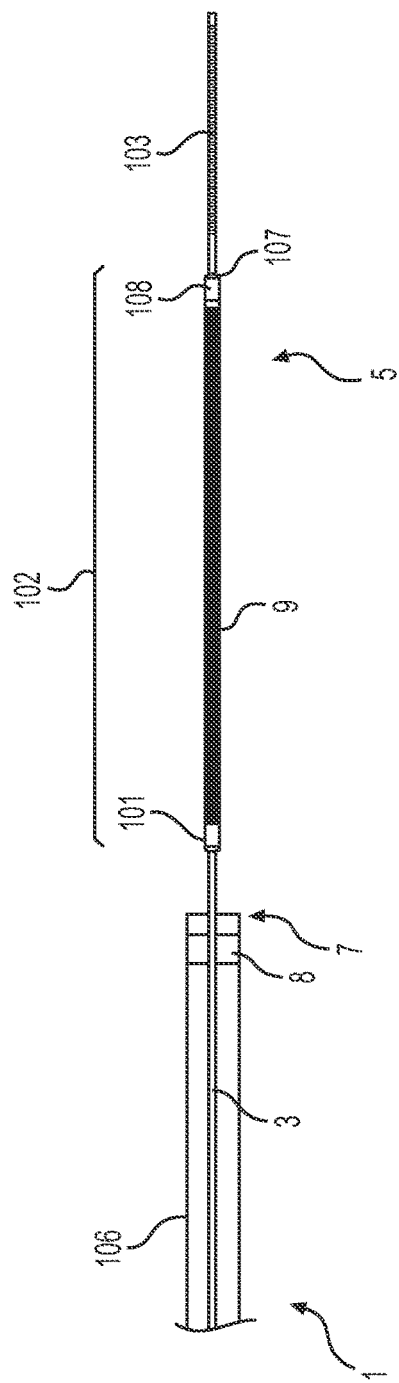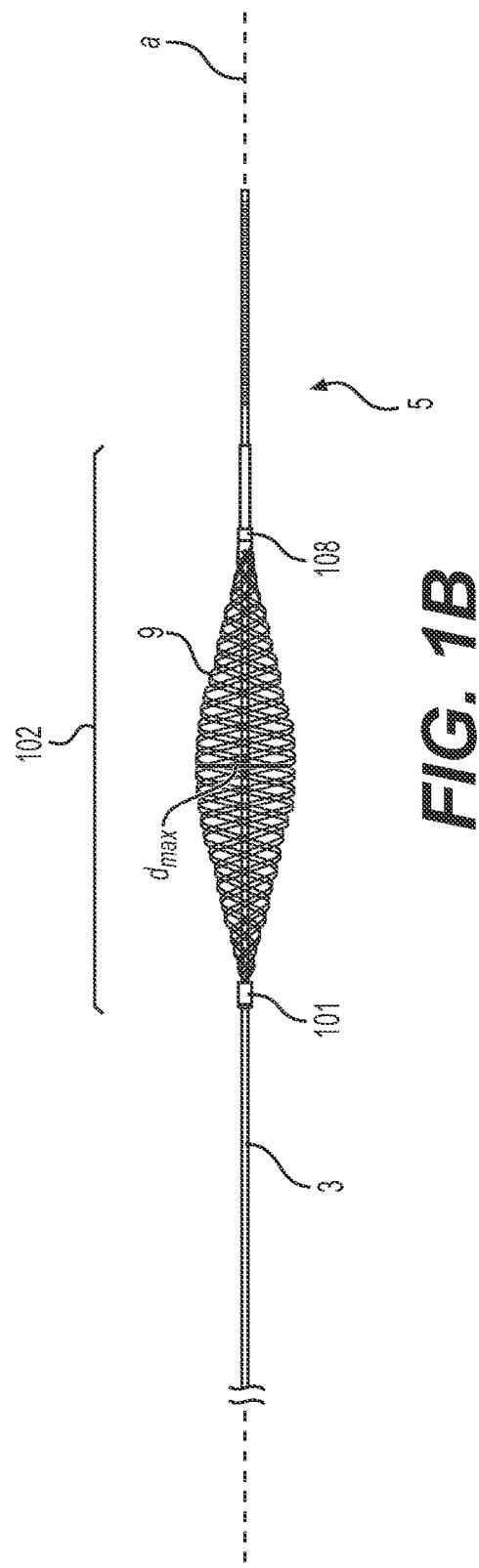
FIG. 1A
FIG. 1B

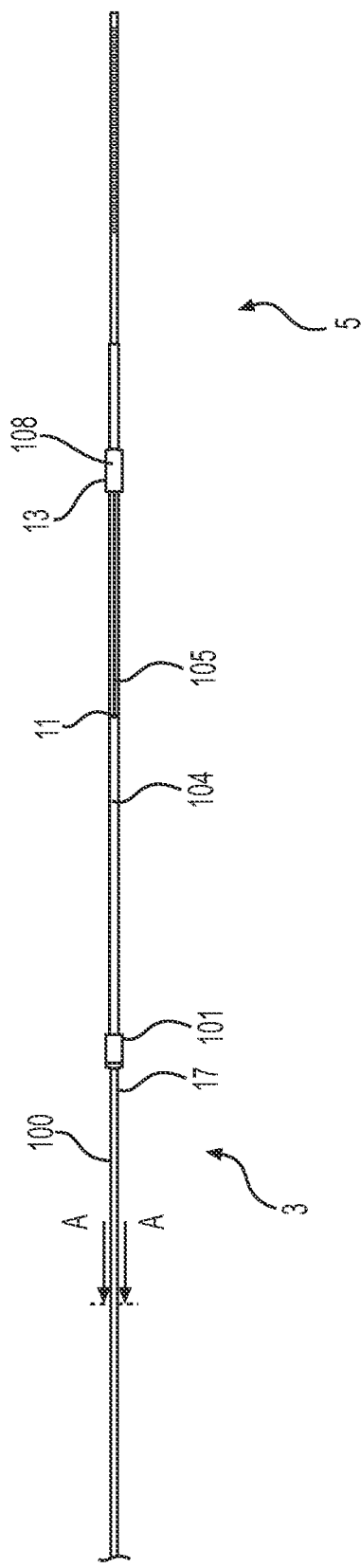
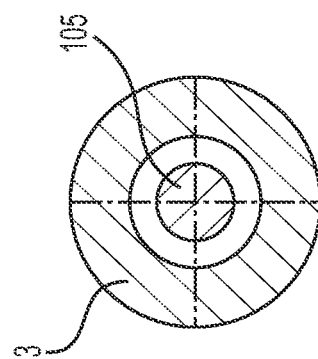
FIG. 1C
FIG. 1D

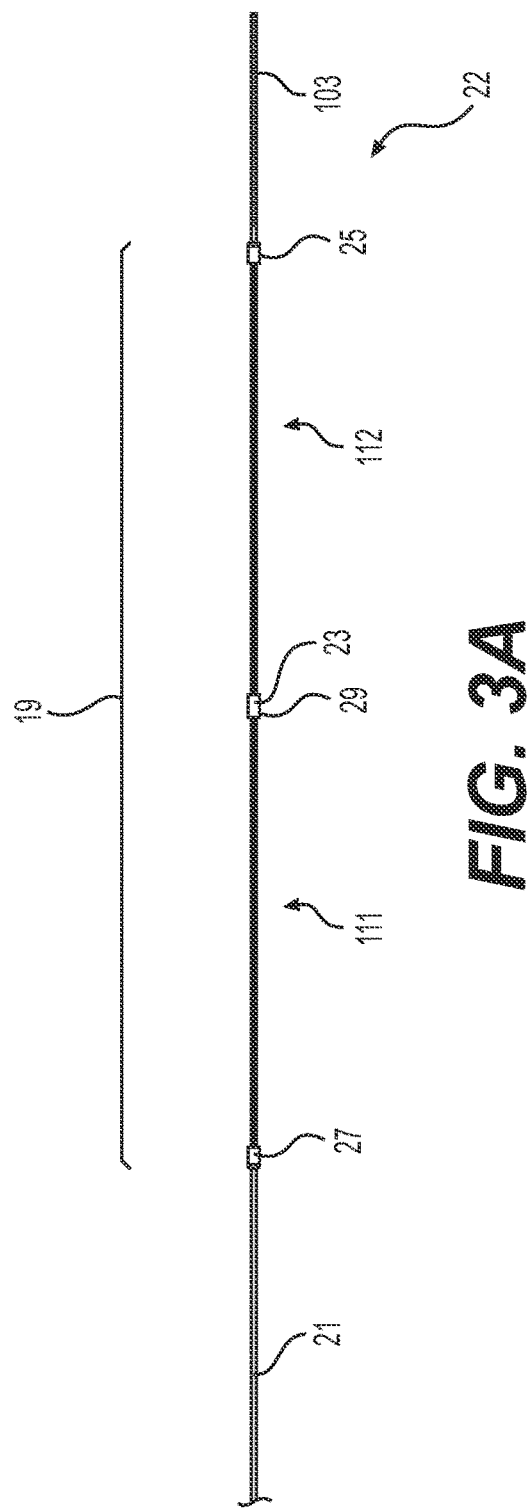
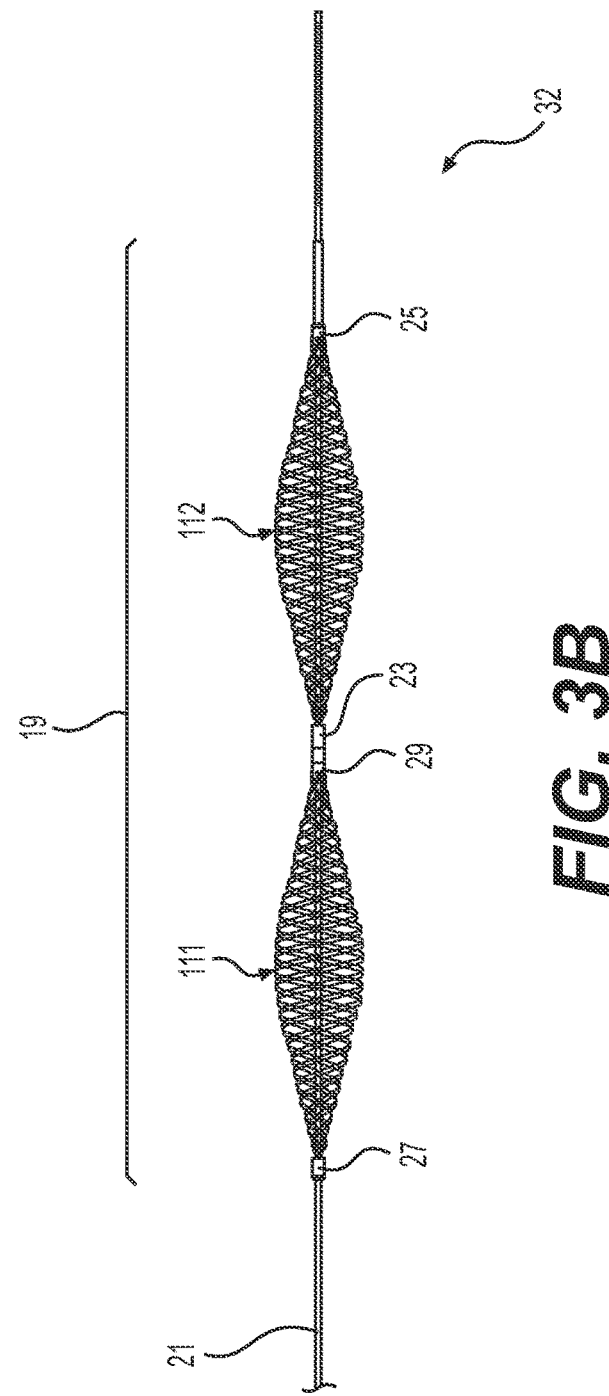

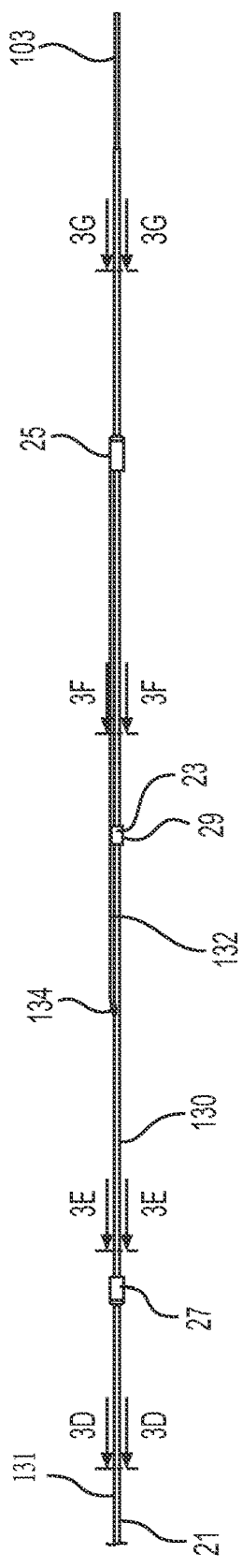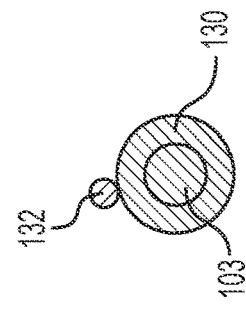

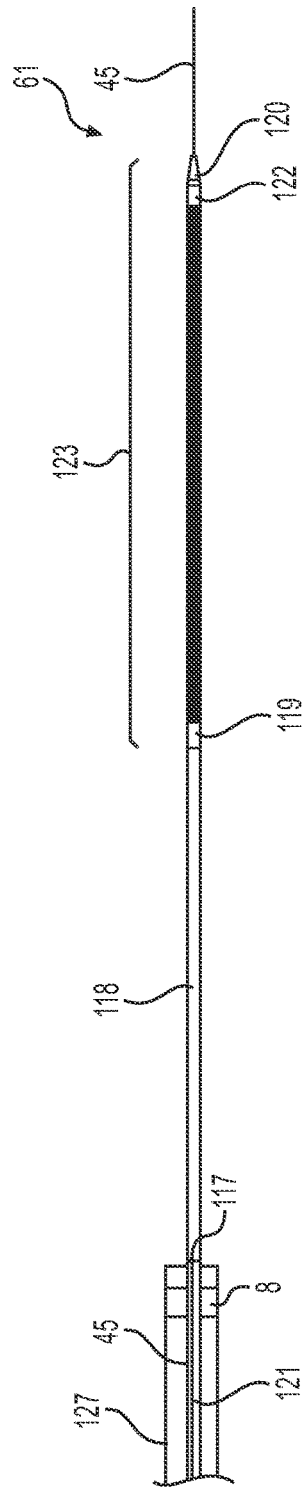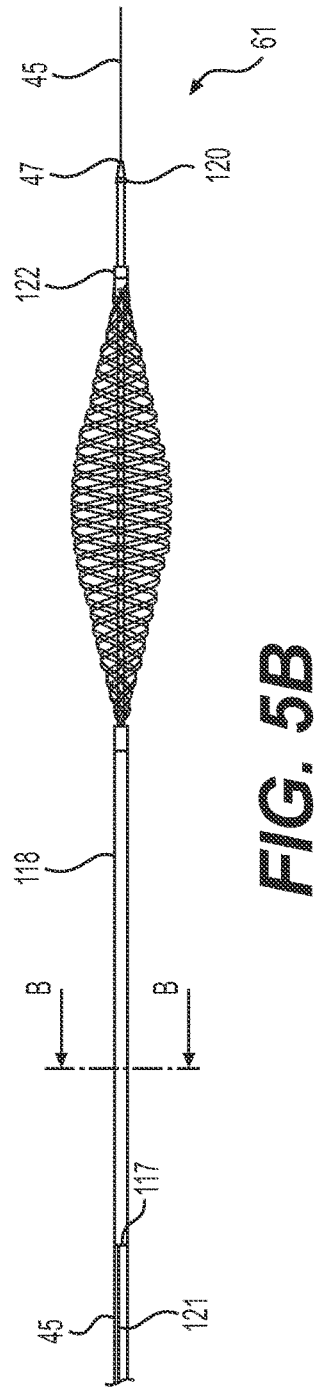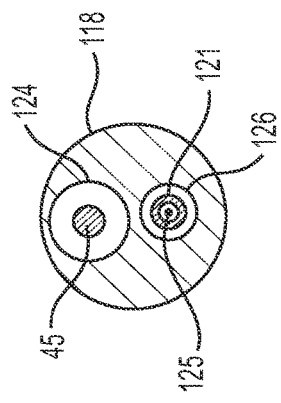
FIG. 5A
FIG. 5B
FIG. 5C

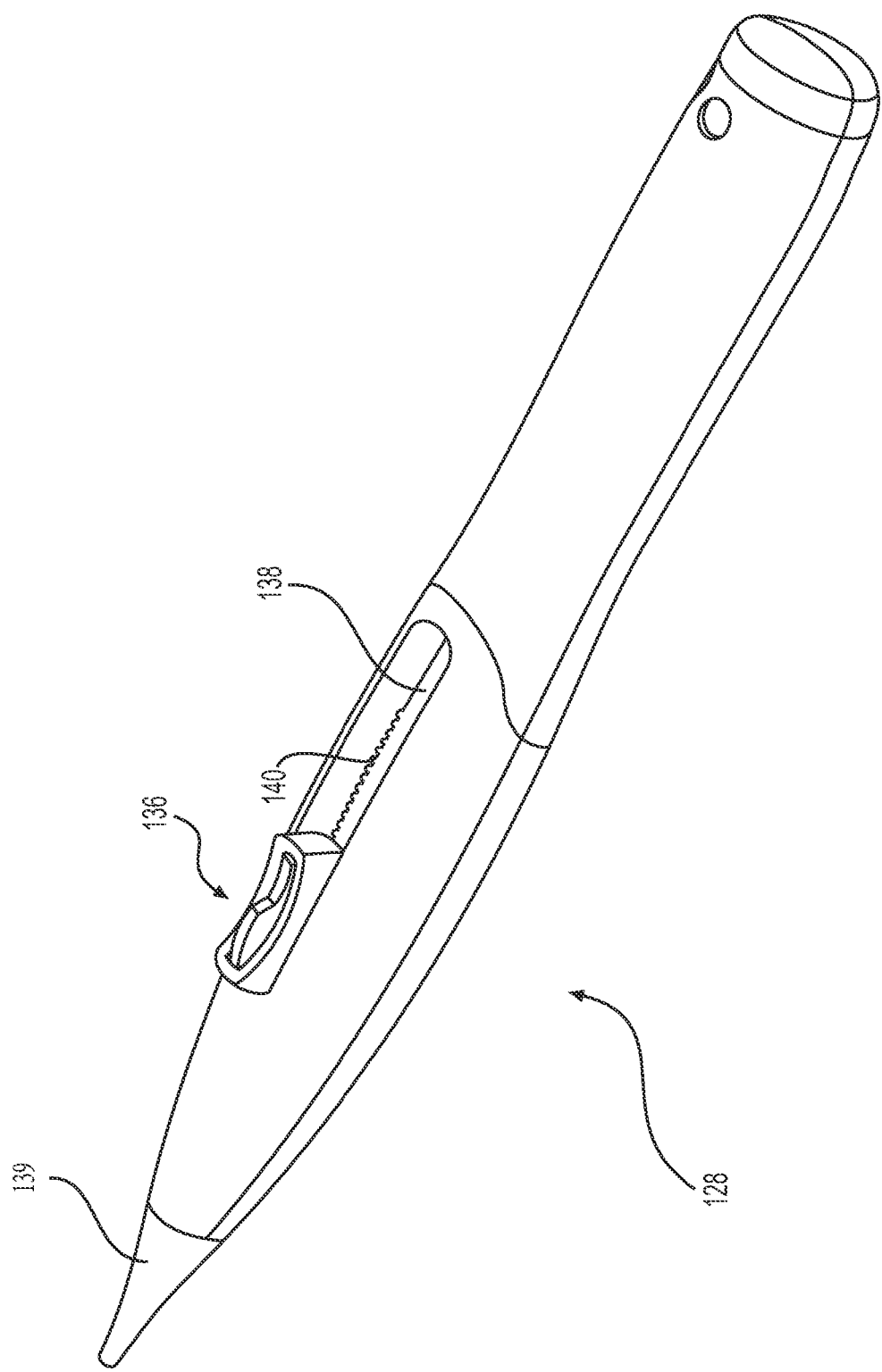

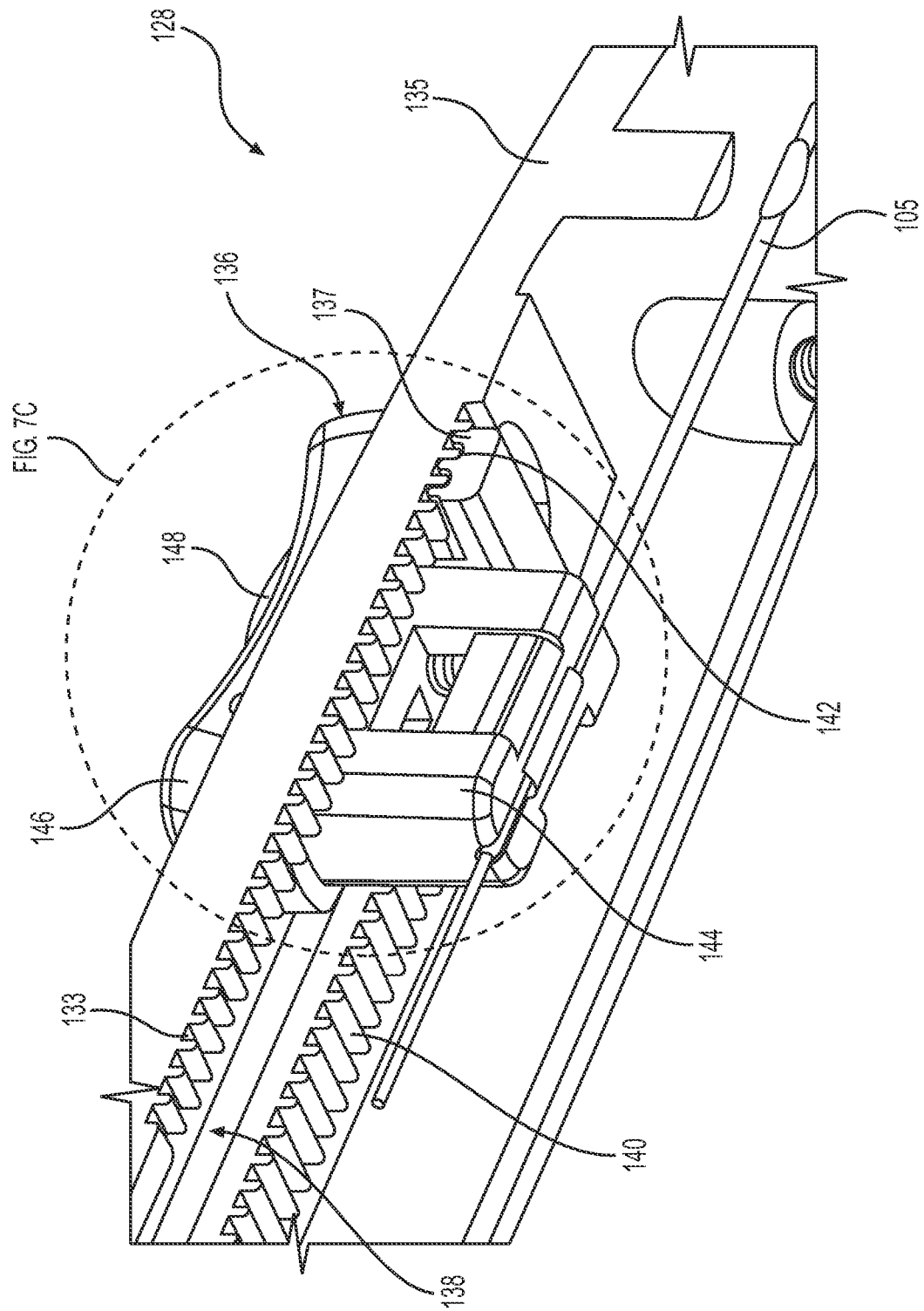

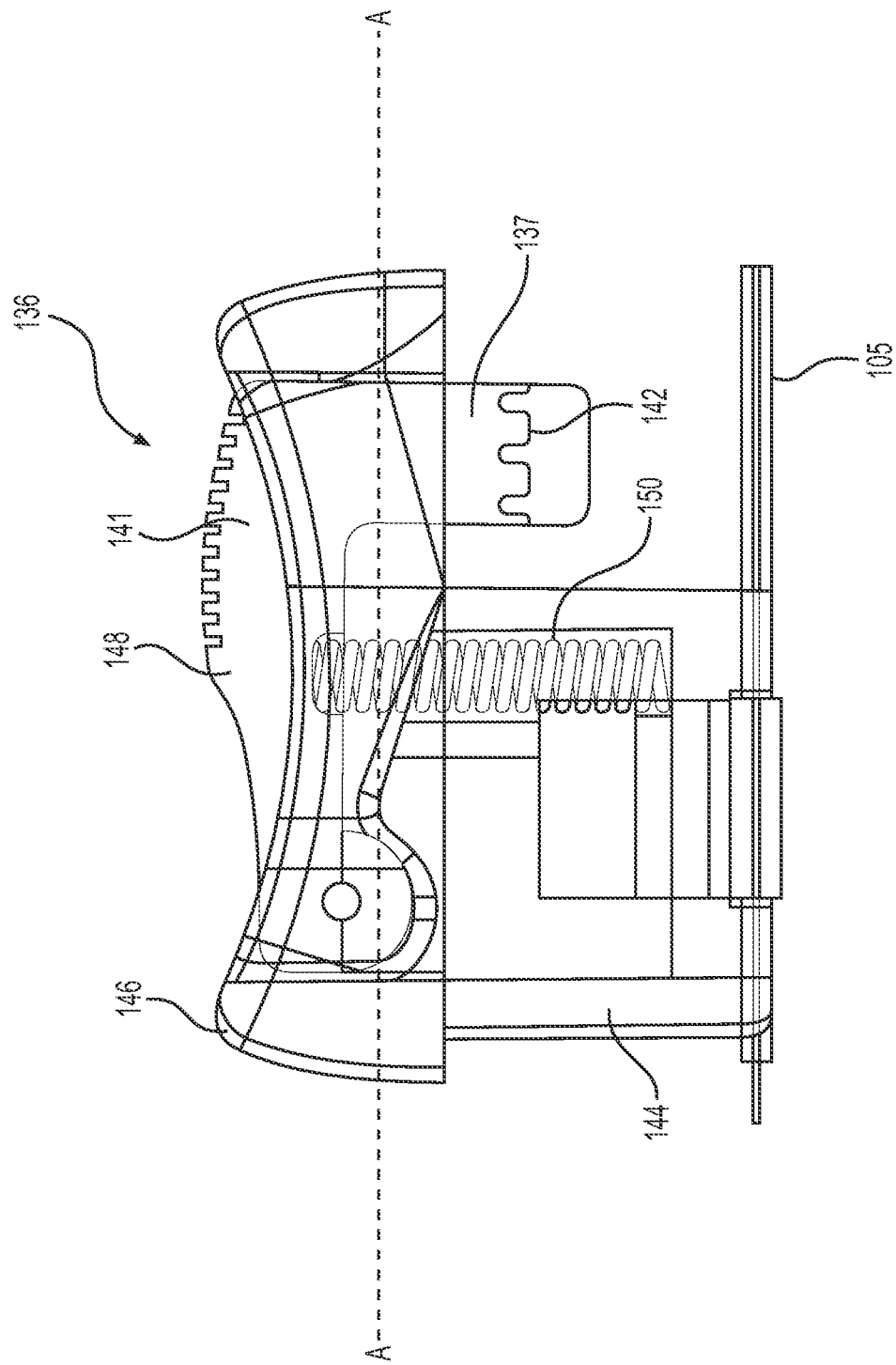

THROMBECTOMY AND ASPIRATION SYSTEM AND METHODS OF USE

RELATED APPLICATIONS

This application claims priority to U.S. Provisional Patent Application No. 63/303,710, filed Jan. 27, 2022, which is hereby incorporated by reference in its entirety.

FIELD

This invention relates generally to medical devices for the removal of tissue from the body, for example, the removal of blood clots (thrombus) or plaque from arteries or veins.

BACKGROUND

It is often desirable to remove tissue from the body in as minimally invasive a manner as possible so as not to damage other tissues. For example, removal of tissue (e.g., blood clots) from the vasculature may improve patient conditions and quality of life.

Many vascular system problems stem from insufficient blood flow through blood vessels. One cause of insufficient or irregular blood flow is a blockage within a blood vessel referred to as a blood clot (or thrombus). Thrombi can occur for many reasons, including after a trauma (such as surgery) or other causes. For example, a large percentage of the more than 1.2 million heart attacks in the United States are caused by blood clots (thrombi) which form within a coronary artery.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery. This results in a shortage of oxygen carrying red blood cells to the muscle (myocardium) of the heart wall. Such a thrombosis can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen. Similarly, thrombosis of one of the carotid arteries can lead to stroke because of insufficient oxygen supply to vital nerve centers in the cranium.

Clinical data indicates that clot removal may be beneficial or even necessary to improve outcomes. For example, in the peripheral vasculature, inventions and procedures can reduce the need for an amputation by 80 percent. The ultimate goal of any modality to treat these conditions of the arterial or venous system is to remove the blockage, thereby restoring patency quickly, safely, and cost effectively. This may be achieved by thrombus dissolution, fragmentation, thrombus aspiration, or a combination of these methods.

Catheter directed thrombectomy and thrombolysis are commonly perceived to be less traumatic and less likely to decrease the morbidity and mortality associated with conventional surgical techniques. In recent years, direct administration of chemical lysing agents into the coronary arteries has shown to be of some benefit to patients who have thrombosed coronary arteries. In this procedure, a catheter is placed immediately in front of the blockage and a drip of streptokinase is directed at the upstream side of the thrombus. Streptokinase is an enzyme which is able to dissolve fibrin. This procedure can take several hours and is not always successful in breaking up the thrombus. Furthermore, it can lead to downstream thrombus fragments (emboli) which can lead to blockage of small diameter branches.

Thrombectomy is a technique for mechanical removal of blood clots in an artery or vein. It refers to physically removing a clot as opposed to employing chemical lysis to dissolve it. Multiple devices have been introduced to break up and remove clot and plaque, but each has its own shortcomings. Specifically, the existing systems do not provide adequate methods for breaking up the clot into smaller pieces for subsequent aspiration. Also, they do not provide a method for removing the thrombectomy device over a guidewire and reinserting into the same location to complete the procedure. Furthermore, the thrombectomy devices of some conventional systems suffer from inversion, a problem where the thrombectomy device folds in on itself during the procedure instead of breaking off thrombus. There is a need for an improved thrombectomy device that is more effective for removing thrombus and plaque from the vascular system.

SUMMARY

The thrombectomy devices, systems and methods disclosed herein facilitate efficient removal of thrombus by increasing the open aspiration area of the distal end, introducing scraping and macerating features to help dislodge the thrombus, increasing the force applied to a thrombus, resisting inversion, and at least partially blocking blood flow during the procedure.

Some thrombectomy devices, systems, and methods include an aspiration catheter comprising a proximal end and a beveled distal end. Some embodiments include a circumferentially extending blocking element coupled to an outer surface of the aspiration catheter, adjacent to the beveled distal end.

In some embodiments, the beveled distal end of the aspiration catheter can have an uneven edge. In some embodiments, the angle of the edge can remain constant traveling proximally along the edge. In others, the angle of the edge can increase traveling proximally along the edge. The beveled distal end can include a material distinct from the material of the proximally situated portions of the aspiration catheter.

The blocking element can be coupled to the outer surface of the aspiration catheter along a blocking element fixation line. In some embodiments, the blocking element fixation line is sloped to approximate an angle of an edge of the beveled distal end. The blocking element fixation line can be, for example, a distance of from 0 millimeters to 10 millimeters distal to the edge of the beveled distal end. The blocking element can extend outward farther from a first side of the aspiration catheter than from a second side of the aspiration catheter. In some embodiments, the blocking element is a balloon.

Some thrombectomy devices, systems and methods disclosed herein include a thrombus retrieval device. The thrombus retrieval device can extend through an aspiration catheter and exit the distal end of the aspiration catheter. The retrieval device includes a proximal region, a distal region, and a first lumen extending between the proximal and distal regions. An activation wire extends through the first lumen of the retrieval device. At least one braided assembly is coupled to the distal region of the retrieval device and to the activation wire. The braided assembly is expandable to a range of expanded outer diameters by varying the level of tension in the activation wire. In some embodiments, the braided assembly includes a braid and a one or more circumferentially extending, oscillating rings encircling the braid. In some embodiments, an expander, such as a balloon, is positioned between the retrieval device and the braided assembly to exert an outward expansion force upon the braided assembly.

The braided assembly can include a braid coupled to a slidable collar. The slidable collar encircles the retrieval device. The braid, which can have a shape memory of a collapsed configuration, extends from the slidable collar toward a fixed attachment point that anchors the braid to the retrieval device. In some embodiments, the activation wire exits the first lumen of the retrieval device via an exit point located on the distal region of the retrieval device and attaches to the slidable collar. The braid can include a plurality of flat wires, a plurality of round wires, or a mixture thereof. In some embodiments, the braided assembly can include one or more circumferentially extending, oscillating rings encircling the braid. The oscillating rings can expand with the braided assembly. The oscillating rings can have a flat surface.

The retrieval device can include different segments along its length. For example, in one embodiment, the retrieval device comprises a proximal reinforcement segment, a central hypotube, and a distal support tube. The central hypotube can have a lower rigidity than the proximal reinforcement segment, and the distal support tube can have a lower rigidity than the central hypotube. In some examples, the proximal reinforcement segment comprises a lubricious coating.

A proximal end of the retrieval device can be coupled to a handle. In some embodiments, the handle can include a mechanism to lock the braided assembly in a fixed outer diameter. For example, the handle can include a locking slider that permits or prevents longitudinal movement of the activation member. In some embodiments, the handle can include a first set of teeth and the locking slider can include a second set of teeth. The first set of teeth can engage with the second set of teeth to place the locking slider in a locked configuration, and the first set of teeth can disengage with the second set of teeth to place the locking slider in a slidable configuration.

Methods of performing thrombectomy procedures are also disclosed herein. The methods can include advancing an aspiration catheter into the vasculature. In some example methods, a guidewire can be advanced to a position distal to the thrombus. The methods can further include advancing a distal end of a retrieval device out of the distal end of the aspiration catheter and to a position distal to the thrombus, pulling the thrombus toward the distal end of the aspiration catheter using the retrieval device, and aspirating the thrombus into the aspiration catheter.

In some example methods, advancing an aspiration catheter includes advancing the retrieval device through a seal of the aspiration catheter hub. Some methods further including sliding a lubricious coating of the retrieval device longitudinally against the seal of the aspiration catheter hub.

In some embodiments, the distal end of the aspiration catheter is beveled. In such embodiments, the methods include advancing the beveled distal end of an aspiration catheter through the vasculature to an area proximal to a thrombus. In some example methods, advancing the beveled distal end of the aspiration catheter further includes contacting the thrombus with the beveled distal end to at least partially dislodge the thrombus.

The methods can further include at least partially blocking fluid flow within the vasculature. At least partially blocking fluid flow within the vasculature can further include expanding a blocking element from the outer surface of the aspiration catheter, for example, by inflating a blocking balloon. In some example methods, expanding a blocking element can include pressing an outer surface of the aspiration catheter against a side of the vasculature. In some example methods, at least partially blocking fluid flow within the vasculature can include selectively blocking one vessel of a bifurcation or trifurcation.

In some example methods, the retrieval device carries at least one braided assembly. A first level of tension is placed into an activation wire that attaches to the braided assembly, thereby deploying the braided assembly to a first expanded outer diameter. Next, a second level of tension is placed into the activation wire, thereby deploying the braided assembly to a second expanded outer diameter. In some example methods, an expander, such as a balloon, can be deployed beneath the braided assembly to exert an outward expansion force upon the braid. The thrombus is contacted with the braided assembly and pulled proximally toward the distal end of the aspiration catheter using the braided assembly. The thrombus is aspirated into the distal end of the aspiration catheter, and the braided assembly is collapsed. The retrieval device can optionally be returned to the thrombus to retrieve any pieces of the thrombus that still remain. Once the thrombus has been satisfactorily removed, the retrieval device and aspiration catheter are withdrawn from the vasculature.

Some examples of the methods of performing a thrombectomy procedure include scraping the thrombus to help dislodge it. In some example methods, the thrombus is scraped with wires of a braid. At least a portion of the wires of the braid can be flattened in shape, and the methods can further include macerating or shaving the thrombus with the flat wires. In some example methods, the thrombus is scraped with a ring that encircles the braid. Collapsing the braided assembly includes a step of folding the ring. Some method examples include clearing a clog within the aspiration catheter by macerating the clog with flattened wires of a braid of the braided assembly.

In some method examples, placing a first level of tension into an activation wire includes moving the activation wire longitudinally within a lumen of the retrieval device, and placing a second level of tension into an activation wire includes moving the activation wire longitudinally within the lumen of the retrieval device. Some method examples include contacting the thrombus with the braid when the braided assembly is expanded to the first expanded outer diameter, then placing a greater second level of tension into the activation wire to open the braided assembly to the wider second expanded outer diameter to more firmly contact the thrombus with the braid. In some method examples, deploying the braided assembly to a first expanded outer diameter includes using the activation wire to move a slidable collar of the braided assembly longitudinally over an exterior surface of the retrieval device, and deploying the braided assembly to a second expanded outer diameter includes using the activation wire to move the slidable collar of the braided assembly longitudinally over the exterior surface of the retrieval device.

In some method examples, the braided assembly can be locked in a fixed outer diameter, for example, by using a locking slider to prevent longitudinal movement of the activation member or activation wire. Using the locking slider can include engaging a first set of teeth with a second set of teeth. The activation member and braided assembly can be unlocked by disengaging the first set of teeth from the second set of teeth, in some examples. The methods can further include retracting the braided assembly while it is locked in the fixed outer diameter.

DESCRIPTION OF DRAWINGS

The device is explained in even greater detail in the following drawings. The drawings are merely exemplary and certain features may be used singularly or in combination with other features. The drawings are not necessarily drawn to scale.

FIG. 1A is a side section view of an embodiment of the thrombectomy device having a single braided assembly in the collapsed configuration.

FIG. 1B is a side view showing the distal region of thrombus retrieval device the thrombectomy device carrying the braided assembly of FIG. 1A. The braided assembly is shown in an expanded configuration.

FIG. 1C is a side view showing the distal region of the thrombectomy device retrieval device of FIG. 1A. The braided assembly is not included in this view.

FIG. 1D is a cross sectional view of the embodiment of FIG. 1A, taken along lines A-A of FIG. 1C.

FIG. 3A is a side view of a distal region of an additional embodiment of the thrombectomy device in an unexpanded configuration. The embodiment has a braided assembly having multiple braided sections.

FIG. 3B is a side view of the distal region of the embodiment of FIG. 3A in an expanded configuration.

FIG. 3C is a side view of the distal region of the thrombectomy device of FIG. 3A. The braided assembly is not included in this view.

FIG. 3D shows a cross sectional view taken along line 3D-3D of FIG. 3C.

FIG. 3E shows a cross sectional view taken along line 3E-3E of FIG. 3C.

FIG. 3F shows a cross sectional view taken along line 3F-3F of FIG. 3C.

FIG. 3G shows a cross sectional view taken along line 3G-3G of FIG. 3C.

FIG. 5A shows a side section view of an embodiment of the thrombectomy device that enables use with a guidewire.

FIG. 5B shows the embodiment of FIG. 5A in an expanded configuration.

FIG. 5C is a cross section of the embodiment of FIGS. 5A and 5B, taken along line B-B of FIG. 5B.

FIG. 7A shows a perspective view of another embodiment of a handle that can be used to control expansion and retraction of a braided assembly.

FIG. 7B shows a bottom up, inside view of the locking slider of the handle embodiment of FIG. 7A.

FIG. 7C shows a cross section of the locking slider circled in FIG. 7B.

DETAILED DESCRIPTION

Figure 2:
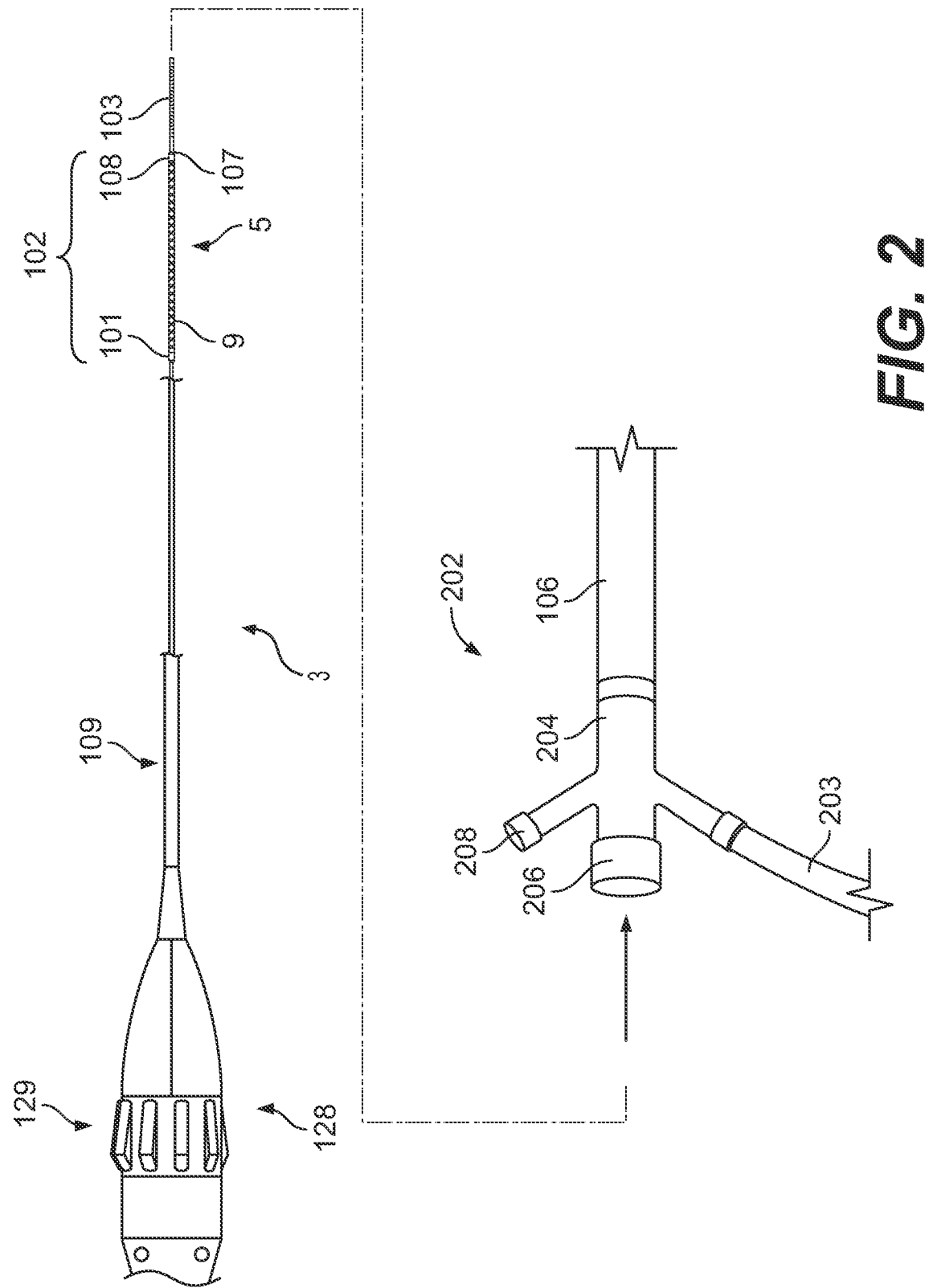
FIG. 2 shows a side view of a handle, retrieval device, braided assembly, and aspiration catheter hub. The straight arrow indicates the direction of insertion of the braided assembly and guidewire tip through the aspiration catheter hub.

The following description of certain examples of the inventive concepts should not be used to limit the scope of the claims. Other examples, features, aspects, configurations, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain advantages and novel features of the aspects and configurations of this disclosure are described herein. The described methods, systems, and apparatus should not be construed as limiting in any way. Instead, the present disclosure is directed toward all novel and nonobvious features and aspects of the various disclosed aspects, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the operations of exemplary aspects of the disclosed method may be described in a particular, sequential order for convenient presentation, it should be understood that disclosed aspects can encompass an order of operations other than the particular, sequential order disclosed. For example, operations described sequentially may in some cases be rearranged or performed concurrently. Further, descriptions and disclosures provided in association with one particular aspect or implementation are not limited to that aspect or implementation, and may be applied to any aspect or implementation disclosed. It will understood that various changes and additional variations may be made and equivalents may be substituted for elements thereof without departing from the scope of the invention or the inventive concept thereof. Certain aspects and features of any given aspect may be translated to other aspects described herein. In addition, many modifications may be made to adapt a particular situation or device to the teachings of the invention without departing from the essential scope thereof. Therefore, it is intended that the invention not be limited to the particular implementations disclosed herein, but that the invention will include all implementations falling within the scope of the appended claims.

Features, integers, characteristics, compounds, chemical moieties, or groups described in conjunction with a particular aspect, configuration, embodiment or example of the invention are to be understood to be applicable to any other aspect, configuration, embodiment, or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing aspects. The invention extends to any novel one, or any novel combination, of the features disclosed in this specification (including any accompanying claims, abstract, and drawings), or to any novel one, or any novel combination, of the steps of any method or process so disclosed.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. The terms "about" and "approximately" are defined as being "close to" as understood by one of ordinary skill in the art. In one non-limiting aspect the terms are defined to be within 10%. In another non-limiting aspect, the terms are defined to be within 5%. In still another non-limiting aspect, the terms are defined to be within 1%.

"Optional" or "optionally" means that the subsequently described event or circumstance may or may not occur, and that the description includes instances where said event or circumstance occurs and instances where it does not.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

Certain terminology is used in the following description for convenience only and is not limiting. The words "right," "left," "lower," and "upper" designate direction in the drawings to which reference is made. The words "inner" and "outer" refer to directions toward and away from, respectively, the geometric center of the described feature or device. The words "distal" and "proximal" refer to directions taken in context of the item described and, with regard to the instruments herein described, are typically based on the perspective of the practitioner using such instrument, with "proximal" indicating a position closer to the practitioner and "distal" indicating a position further from the practitioner. The terminology includes the above-listed words, derivatives thereof, and words of similar import.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The thrombectomy devices disclosed herein remove a thrombus using a braided assembly that can be expanded to a diameter of the practitioner's choosing, enabling the practitioner to custom fit the device to the particular vessel and thrombus and during the procedure. Unlike conventional thrombectomy devices, the diameter of the disclosed braided assembly can be changed mid-procedure as needed. For example, the braided assembly can be opened to a wider diameter to apply more outward force against the thrombus should additional grip be needed for its removal. In some embodiments, multiple braided assemblies can be used to address longer thrombi. Each braided assembly can be separately expanded, such that the individual assemblies have different diameters during the procedure.

Thrombectomy devices and methods of use are described in International Publication No. 2019/094749, which is incorporated by reference herein. The device disclosed herein is used to the remove a thrombus, clot, or plaque from the veins or arteries of the body. It includes an aspiration catheter and a retrieval device that extends through the lumen of the aspiration catheter. The aspiration catheter can connect at its proximal end to an aspiration system and vacuum source. Example aspiration systems and methods of use are described in International Publication No. 2022/231966, which is incorporated by reference herein. An expandable braided assembly extends over a distal region of the retrieval device, such that when the retrieval device exits the distal end of the aspiration catheter, the braided assembly is positioned outside of the aspiration catheter. An activation wire extends through the lumen of the retrieval device. The distal end of the activation wire exits the retrieval device at an exit point to connect to and control the expansion of a braided assembly. On the proximal end, the activation wire is attached to a tensioning element. Applying tension to the activation wire causes the braided assembly to expand to a diameter of the practitioner's choosing. For example, the practitioner may apply a first level of tension to deploy the braided assembly to a first, partially expanded configuration and then later decide to widen the diameter to the fully expanded configuration by applying a greater level of tension to the activation wire. The expanded braided assembly contacts the thrombus, clot, or plaque and is pulled proximally toward the aspiration catheter to assist in removal. Hereinafter the device and methods will be described as removing (or being configured to remove) a thrombus. However, it will be understood that the device can also be used to remove clots or plaques from the vasculature with no structural (or only slight structural) modifications. Various embodiments of the thrombectomy catheter include a retrieval device with multiple braided assemblies, multiple activation wires, multiple braided sections of a single braided assembly, and retrieval devices with multiple lumens to, for example, enable use with a guidewire.

FIGS. 1A-1D show an embodiment of the thrombectomy device 1. FIG. 1A shows the aspiration catheter 106, the thrombus retrieval device 3, a collapsed braided assembly 102, and a guidewire tip 103. The aspiration catheter 106 is an elongated tube with reinforced construction that allows a vacuum to be applied at the proximal end to pull clot and emboli out of the artery or vein without collapsing. The aspiration catheter 106 can be formed of a polymer material. The aspiration catheter 106 can include an imaging marker 8 (such as a fluorescent or radiopaque marker) for use in imaging the position of the catheter during a procedure. Thrombus retrieval device 3 extends through aspiration catheter 106. The braided assembly 102 extends over a distal region 5 of the retrieval device 3, such that when the retrieval device 3 exits the distal end 7 of the aspiration catheter 106, the braided assembly 102 is positioned outside of the aspiration catheter 106. In the collapsed configuration, braided assembly 102 is sized and configured for insertion through the aspiration catheter 106 and into an artery or vein. Guidewire tip 103 extends distally from the distal end 107 of the retrieval device 3. The guidewire tip 103 can be flexible, shapeable, and steerable.

The braided assembly 102 is moveable from a collapsed to an expanded configuration. An example of a braided assembly 102 in an expanded configuration is shown in FIG. 1B, but the maximum diameter, $d_{max}$, of the expanded braided assembly 102 can be changed to any value over a continuous range, from a fully collapsed diameter, to a partially expanded diameter, to a fully expanded diameter. The maximum diameter of the braided assembly, $d_{max}$, is the widest point measured perpendicular to a longitudinal axis, a, extending through the center of the braided assembly 102. The braided assembly 102 can be sized and configured to disrupt and capture one or more clots, plaques, and/or thrombi and pull them toward the aspiration catheter 106 where they can be removed. The braided assembly 102 includes a braid 9, a slidable collar 108, and a fixed attachment point 101 where the braid 9 anchors to the retrieval device 3. The braid 9 may be attached directly to the retrieval device 3 at attachment point 101, or the braid 9 may be attached indirectly to the retrieval device 3 at attachment point 101. In some embodiments, the fixed attachment point 101 is a fixed collar that extends around the retrieval device 3, and the braid is welded, bonded, or otherwise adhered to the fixed collar. Regardless, at the fixed attachment point 101, the braid 9 does not move longitudinally relative to the retrieval device 3.

The opposite end of braid 9 is welded, bonded, or otherwise adhered to slidable collar 108. In the embodiments shown, the slidable collar 108 is slidably connected to the retrieval device 3 by virtue of its annular shape, which extends circumferentially around the retrieval device 3. The slidable collar 108 slides longitudinally along the retrieval device 3 as braid 9 is expanded and collapsed. The slidable collar 108 can be positioned distally to the fixed attachment point 101 (a distal position), as shown in FIGS. 1A-1C, or the slidable collar 108 can be positioned proximally to the fixed attachment point 101 (a proximal position). In some embodiments, slidable collar 108 or fixed attachment point 101 can include a marker that can be viewed using imaging modalities during a procedure. For example, the slidable collar 108 or fixed attachment point 101 can include a fluorescent or radiopaque label.

The braid 9 is composed of multiple strands of wire. The braid 9 takes an elliptical or a spindle shape when expanded, having a maximum diameter $d_{max}$ at or near the center of the braid 9 and narrowing as the braid approaches the fixed attachment point 101 and the slidable collar 108. The wires are formed of a shape memory material such as, but not limited to, shape memory polymers or shape memory metals (e.g., nitinol). The braid 9 has a baseline shape memory of the collapsed configuration, which forms a cylindrical structure around the retrieval device 3, as shown in FIG. 1A. In the activated, expanded configuration, the braid 9 has a tendency to relax toward the collapsed configuration.

When the practitioner is pulling a thrombus or plaque proximally toward aspiration catheter 106 using braided assembly 102, the braid 9 encounters distally oriented drag forces that are strongest along the widest portions (for example, the central region of the braid adjacent $d_{max}$) These drag forces resist the proximally oriented pulling force exerted by the practitioner. The distal end of braid 9 at slidable collar 108 will encounter less drag force while being pulled proximally because the radial force it exerts on the radially adjacent vasculature or thrombus is small, negligible, or non-existent. If the braid is not properly designed, the sliding collar 108 and distal end of the braid 9 will invert into the wider, central regions of the braid 9. Inversion during the procedure can be prevented by optimizing factors such as the pic count (crosses per inch), the wire diameter, the number of wires, and the ply of the braid (sets of overlapping braids). Higher pic counts increase flexibility, while lower pic counts increase longitudinal stiffness. Likewise, a braid with more than one ply (multiple sets of braids nested within each other), will be stiffer than a single-ply braid. Braids can be one-ply, two-ply, three-ply, or more. Braids with more wires will be stiffer than those with fewer wires, and braids with wider diameter wires will be stiffer than those with narrow diameter wires. Wires of varying diameters can be used within the same braid 9.

The design of the braided assemblies 102 disclosed herein may vary based on whether the device 1 is intended for an arterial procedure or for a venous procedure, since the procedure site will be wider in a venous setting. For example, a braid 9 designed for a venous application may have a $d_{max}$ of from about 0.8 inches to 1.2 inches, including about 0.8 inches, about 0.9 inches, about 1.0 inch, about 1.1 inches, and about 1.2 inches. For venous applications, a braid 9 may have a wire diameter range from about 0.005 inches to about 0.02 inches, including 0.005 inches, 0.0075 inches, 0.01 inches, 0.0125 inches, 0.015 inches, 0.0175 inches, and 0.02 inches. Different wires of the braid 9 may have different diameters, or they may have the same diameter. In some venous embodiments, the diameters of the wires of the braid 9 are 0.01 inches, 0.0125 inches, and/or 0.015 inches. Two-ply braids can utilize smaller wire diameters without sacrificing the radial force that can be applied. The pic count can be from 2 to 6 for venous applications. In some embodiments used in venous applications, the pic count is 3, 4, or 5. The number of wires per braid for a venous application can be anywhere from 8 to 40, including 8, 16, 24, 32, and 40.

Braids for venous applications were tested using a selection of the above listed venous application parameters. End points included the expansion force and the radial outward force applied by the braid to the inner surface of a tubing that simulates a vein (the tubing having an inner diameter of 24 millimeters). The expansion force is the force required to open the braid, as applied to the activation wire. The data is shown below in Table 1.

TABLE 1

Prototype testing for braids used in venous applications

| Prototype | Braid Ply | Wire Diameter (Inches) | # of Wires | Maximum Braid OD (inches) | Radial Outward Force in 24 mm ID tube (N) | Expansion force (N) |
|---|---|---|---|---|---|---|
| A | Double | 0.008 | 16 per ply (32 total) | 1.0 | 4.4 | 2.5 |
| B | Double | 0.010 | 16 per ply (32 total) | 1.0 | 5.5-6.6 | 6 |
| C | Single | 0.0125 | 24 | 1.0 | 8.6-9.9 | 10 |

For arterial applications, the braid 9 can have $d_{max}$ of from about 0.1 inches to about 0.4, including about 0.1 inches, about 0.12 inches, about 0.14 inches, about 0.18 inches, about 0.2 inches, about 0.22 inches, about 0.24 inches, about 0.28 inches, about 0.3 inches, about 0.32 inches, about 0.34 inches, about 0.36 inches, about 0.38 inches and about 0.4 inches. For example, the braid 9 can have a $d_{max}$ of about 0.28 inches, 0.3 inches, or 0.31 inches. The diameter of the wires of the braid 9 for an arterial application can range from about 0.001 inches to about 0.007 inches, including about 0.001 inches, about 0.002 inches, about 0.003 inches, about 0.004 inches, about 0.005 inches, about 0.006 inches, and about 0.007 inches. Different wires of the braid 9 may have different diameters, or they may have the same diameter. In some arterial embodiments, the diameters of the wires of braid 9 are 0.003 inches, 0.004 inches and/or 0.005 inches. Two-ply braids can utilize smaller wire diameters without sacrificing the radial force that can be applied. The pic count can be from 5 to 30 for arterial applications, including a pic count of 5, 6, 7, 8, 9, 10, 11, 12, 13, 14, 15, 16, 117, 18, 19, 20, 21, 22, 23, 24, 25, 26, 27, 28, 29 and 30. In some embodiments used in arterial applications, the pic count is 10, 12, or 15. The number of wires per braid 9 for an arterial application can be anywhere from 8 to 54, including 8, 16, 24, 32, 40, 48, and 54. In some embodiments, the number of wires per braid 9 for an arterial application is 26, 24, or 30.

Braids for arterial applications were tested using a selection of the above listed arterial application parameters. End points included the radial outward force applied by the braid to the inner surface of a tubing (the tubing having an inner diameter of 6 millimeters), and the proximal force needed to pull the braid through a restriction in the tubing (the inner diameter of the restriction being 4 millimeters). The tubing and the restriction simulate an artery and a thrombus/plaque, respectively. Favorable prototypes give a high radial outward force without requiring excessive force to pull the braid through the restriction. The data is shown below in Table 2. All braids tested were one-ply.

TABLE 2

Prototype testing for braids used in arterial applications

| Prototype | Wire Diameter (inches) | Pic count | # of Wires | Profile (Distal bond OD) (inches) | Maximum Braid OD (inches) | Radial Outward Force applied to 6 mm I.D. tubing (Newtons) | Force to pull through 4 mm ID Restriction (Newtons) |
|---|---|---|---|---|---|---|---|
| A | 0.004 | 10 | 16 | 0.050 | 0.28 | 0.8 | 1.8 |
| B | 0.004 | 15 | 24 | 0.053 | 0.28 | 1.0 | 2.8 |
| C | 0.005 | 10 | 16 | 0.054 | 0.31 | 1.5 | 3.2 |
| D | 0.005 | 10 | 24 | 0.058 | 0.31 | 1.6 | 4.1 |
| E | 0.006 | 10 | 16 | 0.060 | 0.31 | 1.7 | 4.4 |
| F | 0.006 | 12 | 16 | 0.063 | 0.30 | 1.8 | 4.6 |
| G | 0.002 | 24 | 48 | 0.073 | 0.31 | 0.8 | 1.9 |
| H | 0.003 | 24 | 48 | 0.078 | 0.31 | 1.8 | 3.5 |
| I | 0.004 | 12 | 24 | 0.054 | 0.31 | 1.9 | 2.6 |

The activation wire 105 (or activation member 105), extends through the lumen of the retrieval device 3, exits the retrieval device 3 at exit point 11, and extends distally along the exterior surface of the retrieval device 3. The distal end 13 of the activation wire 105 is attached to slidable collar 108. As such, the activation wire 105 is able to control the expansion and collapse of the braid 9 via the slidable collar 108. The distance between exit point 11 and slidable collar 108 affects the length that the slidable collar can be pulled along retrieval device 3 to open the braided assembly 102. If it is too close to slidable collar, the braided assembly 102 will not be able to open fully. As such, exit point 11 should be positioned proximally far enough from the unexpanded position of slidable collar 108 to enable the braided assembly 102 to open to its maximum outer diameter. FIG. 1C shows the embodiment of FIGS. 1A and 1B without braid 9 to facilitate viewing the activation wire 105 and the activation wire exit point 11. FIG. 1D is a cross sectional view of activation wire 105 in retrieval device 3, taken at line A-A of FIG. 1C. The internal positioning of the proximal regions of the activation wire 105 (within retrieval device 3) is advantageous in that no friction or bulk is added by the system that controls expansion of the braided assembly 102.

The proximal region of activation wire 105 (not shown) may be tensioned and released to control the expansion and collapse of the braided assembly 102 via movement of slidable collar 108. Under tension, the activation wire 105 moves proximally within the lumen of the retrieval device 3 as it translates the tension from the proximal region of the activation wire 105 to the braided assembly 102. In implementations where the slidable collar 108 is in the distal position (as shown), the exit point 11 of the activation wire is located proximally to the slidable collar 108. The exit point 11 can be, for example, a portal in the sidewall of retrieval device 3. Use of a slidable collar 108 to expand the braided assembly 102 is advantageous because the distal end of the braided assembly 102 can be moved while the distal region 5 of the retrieval device 3 maintains a constant position within the vasculature. Maintaining a constant position of the distal region 5 of retrieval device 3 is advantageous because sliding proximal/distal movement of the distal region 5 within the vessel can result in vessel damage or perforation.

In implementations where the slidable collar 108 is in the proximal position relative to the fixed attachment point (not shown), the activation wire 105 extends distally past the slidable collar 108 inside the retrieval device 3, exits the retrieval device 3 at exit point 11, then doubles back and extends along the exterior surface of the retrieval device 3 to attach to the proximally located slidable collar 108. The exit point 11 can be a portal in the sidewall of the retrieval device as described above, or the exit point 11 can be the distal end 107 of the retrieval device 3.

Retrieval device 3 can include a proximal reinforcement segment 109, a central hypotube 100, and a distal support tube 104. Central hypotube 100 and distal support tube 104 are shown in FIG. 1C. Embodiments that also include a proximal reinforcement segment 109 will be described below with reference to FIG. 2. In some embodiments, the central hypotube 100 extends through the support tube 104. However, the distal region can be made more flexible by attaching the proximal end of the distal support tube 104 to the distal end 17 of the central hypotube 100 (for example, by adhesive bonding, heat bonding, or welding processes). The fixed attachment point 101 of the braided assembly 102 can be located on distal support tube 104 and the slidable collar 108 can extend around the distal support tube 104, such that the braided assembly 102 is positioned over and around the distal support tube 104. The braided assembly 102 can alternatively be positioned only partially over the distal support tube (i.e., one of the fixed attachment point 101 or the slidable collar 108 is attached to the central hypotube 100, and the other of the fixed attachment point or the slidable collar 108 is attached to the distal support tube 104). In some embodiments, the support tube 104 serves to increase the overall diameter of the retrieval device 3, for example, to accommodate a larger diameter braid and to encapsulate the guidewire tip 103. The distal support tube 104 can also provide a lower friction surface for movement of the slidable collar 108 than the central hypotube 100 would provide.

In some embodiments, distal support tube 104 has greater flexibility (lower rigidity) than the central hypotube 100. For example, the distal support tube 104 can be made of a polymer material, while the central hypotube 100 is made of a more rigid metal material. In some embodiments, the central hypotube 100 is constructed from metal hypodermic needle tubing. The hypotube 100 can be up to 50 times stiffer than the support tube 104. There are several advantages to having a distal support tube 104 with greater flexibility than central hypotube 100. The greater flexibility of the support tube 104 enables a gradual transition in flexibility between the hypotube 100 and the guidewire tip 103. In some scenarios, the greater flexibility of the distal support tube 104 can facilitate movement of the braided assembly 102 through a tortuous thrombus. The greater flexibility can promote kink resistance. The greater flexibility of the distal support tube 104 can also facilitate the introduction of a portal or exit point 11 during the production of the device. The higher rigidity of the hypotube 100 (as compared to support tube 104) is important because it allows the retrieval device 3 to be pushed through the vasculature. The rigidity of hypotube 100 also helps to ensure that the braided assembly 102 can be pushed through a thrombus or plaque.

FIG. 2 shows a proximal handle 128, a retrieval device 3, and a braided assembly 102, with an arrow to indicate the direction of insertion of the braided assembly 102 into an aspiration catheter hub 202. Though FIG. 2 shows aspiration catheter 202 and retrieval device 3 used together, it should be understood that the aspiration catheters disclosed herein can be utilized with other types of thrombus retrieval devices, and that the thrombus retrieval devices disclosed herein can be utilized with other types of aspiration catheters. In FIG. 2, the proximal handle 128 is coupled to a proximal end of retrieval device 3 at proximal reinforcement segment 109. The proximal handle 128 provides a tensioning element, such as knob 129, that moves the activation wire 105 forward or backward within the retrieval device 3. A proximal end of activation wire 105 is coupled to the tensioning element within handle 128. Applying tension to the activation wire 105 causes the slidable collar 108 to move and causes the braided assembly 102 to expand to a diameter of the practitioner's choosing. Similarly, releasing tension on the activation wire 105 allows the braided assembly 102 to relax into the collapsed, baseline configuration. In the example shown in FIG. 2, actuation of the knob 129 in one direction causes the activation wire 105 to be tensioned (thereby expanding the braided assembly), and actuation of the knob 129 in the opposite direction releases tension on the activation wire 105 (thereby collapsing the braided assembly). In other embodiments, the tensioning element can include a slider, racheting mechanism, or lever.

The aspiration catheter hub 202 shown in FIG. 2 is positioned at the proximal end of aspiration catheter 106. Catheter hub 202 includes an adaptor 204 that splits the lumen into at least two paths. A first path leads to aspiration tubing 203, which is connected to a vacuum source for removal of the clot or emboli. A second path allows for introduction of the distal end 5 of retrieval device 3 through proximal port 206. Some embodiments can include a third path with an infusion port 208 for introducing contrast agent or saline. One technical issue here is that in order to allow introduction of the retrieval device 3, the proximal port 206 cannot be fully closed. This causes it to leak either air or blood, especially when retrieval device 3 is introduced through catheter hub 202 alongside a guidewire. To prevent these leaks, the catheter hub 202 can have a variety of seals and/or valves. These seals clamp down on the retrieval device 3 once the distal end and braided assembly are positioned near the thrombus to prevent leaks during the procedure. This clamping down of the catheter hub 202 can hinder lateral movement of the retrieval device 3. To facilitate movement of the retrieval device 3 through a tightly clamped seal of the catheter hub 202, some embodiments of the retrieval device 3 include a proximal reinforcement segment 109. The reinforcement segment 109 is thicker and more rigid than the central hypotube 100. The greater rigidity provides additional column strength over what is offered by central hypotube 100. This additional column strength makes it easier to move retrieval device 3 back and forth through the tightly clamped seal of the catheter hub 202 by pulling and pushing on the handle 129. This back and forth movement translates through the retrieval device 3 to the braided assembly 102, which scrapes thrombus proximally toward the aspiration catheter, then can return to scrape some more thrombus.

In some embodiments, the reinforcement segment 109 runs approximately half the length of the retrieval device 3, but could be less or more depending upon the procedure. In one example, the central hypotube 100 is formed of nitinol, whereas the proximal reinforcement segment 109 can be formed of stainless steel. As another example, the reinforcement segment 109 can be formed of combination of nitinol and stainless steel. As another example, the reinforcement segment 109 can be formed of a nitinol tube that is thicker than a nitinol tube of the central hypotube 100.

In some embodiments, the proximal reinforcement segment 109 can also include a lubricious coating, which reduces friction between the proximal reinforcement segment 109 and the seal of catheter hub 202, making it easier to move the retrieval device 3 and the braided assembly 102 within the vessel. Materials for the lubricious coating can include, for example PTFE.

Another embodiment of a proximal handle 128 is shown in FIGS. 7A-7C. The handle 128 of FIGS. 7A-7C is advantageous in that it enables a practitioner to lock the braided assembly 102 at a fixed outer diameter. This can be useful, for example, when pushing and pulling the device through a thrombus. As shown in FIG. 7A, proximal handle 128 is coupled to a proximal end of retrieval device 3. Activation wire 105 extends proximally past the proximal end retrieval device 3 and into proximal handle 128. Strain relief section 139 is formed of a flexible material that prevents kinking of the retrieval device 3 just distal to the handle 128. Proximal handle 128 also includes a tensioning element in the form of locking slider 136, which slides proximally and distally within groove 138 and can be locked in place to secure the outer diameter of the braided assembly 102 during a procedure. The interior underside of locking slider 136 and groove 138 is shown in FIG. 7B, and a cross sectional view of locking slider and groove 138 is shown in FIG. 7C. Locking slider 136 includes a sliding portion 146 and a lock button 148. As seen in FIG. 7B, downward pointing teeth 140 extend downward from the inner surface 133 of the outer casing 135 of handle 128, from a position adjacent the groove 138. The lock button 148 includes an exterior portion 141 with a textured gripping surface. The lock button 148 extends downward through sliding portion 146, and includes an interior portion 137. The interior portion 137 of the lock button 148 extends away from the exterior portion 141 of lock button 148 in a direction that is perpendicular to the longitudinal axis A-A of the locking slider 136. Interior portion 137 includes upward facing teeth 142 that are configured to engage with the downward facing teeth 140 of the outer casing 135 of the handle 128. Spring 150, which is vertically positioned within slider 146, beneath the exterior surface 141 of lock button 148, exerts an upward force on lock button 148 to hold the upward facing teeth 142 in a locked configuration with the downward facing teeth 140 of the outer casing 135. When lock button 148 is compressed, the spring 150 is compressed and the teeth 140, 142 disengage. With the lock button 148 pressed and the teeth 140, 142 disengaged, proximal or distal force can be applied to sliding portion 146 to move the locking slider 136 within the groove 138. An interior portion 144 of the sliding portion 146 grips the activation wire 105. As the locking slider 136 is moved within groove 138, the activation wire 105 is moved proximally or distally to affect the expansion or allow the collapse of the braided assembly 102.

Figure 20A:
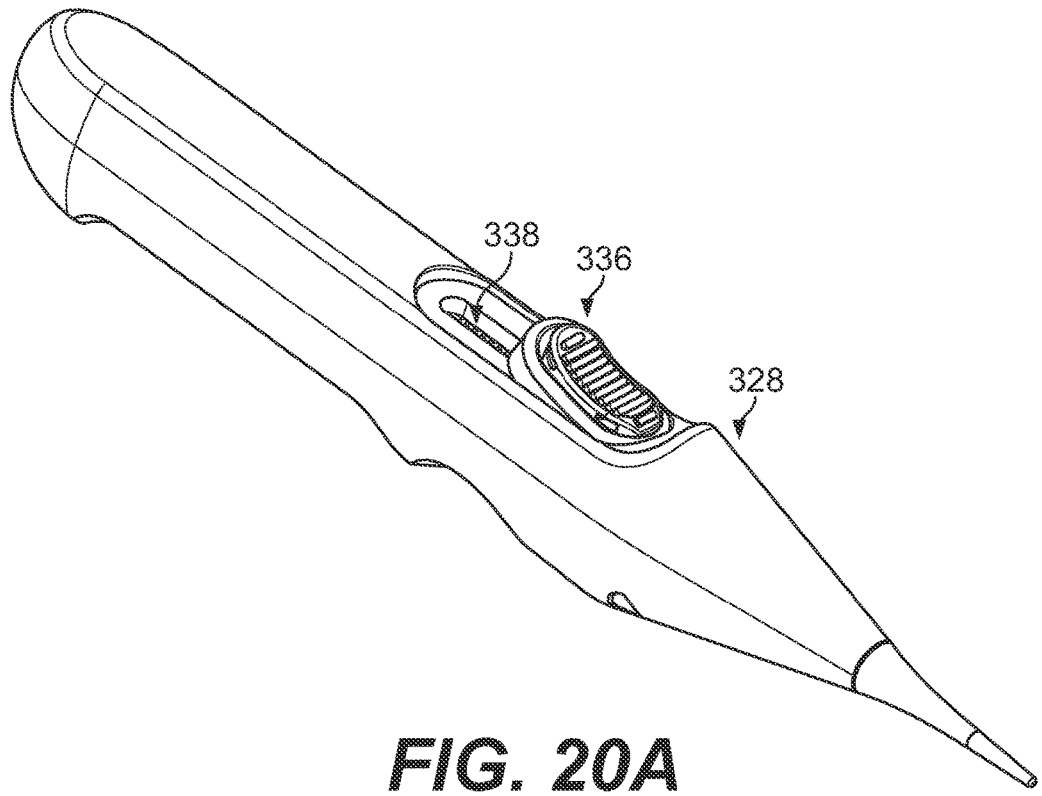
FIG. 20A shows a perspective view of a handle and a locking slider.
Figure 20B:
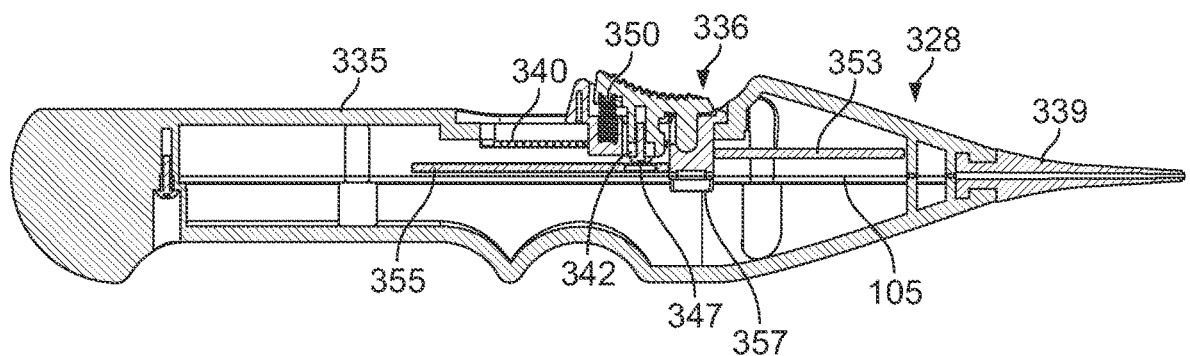
FIG. 20B shows a cross section of the of the handle embodiment of FIG. 20A.
Figure 20C:
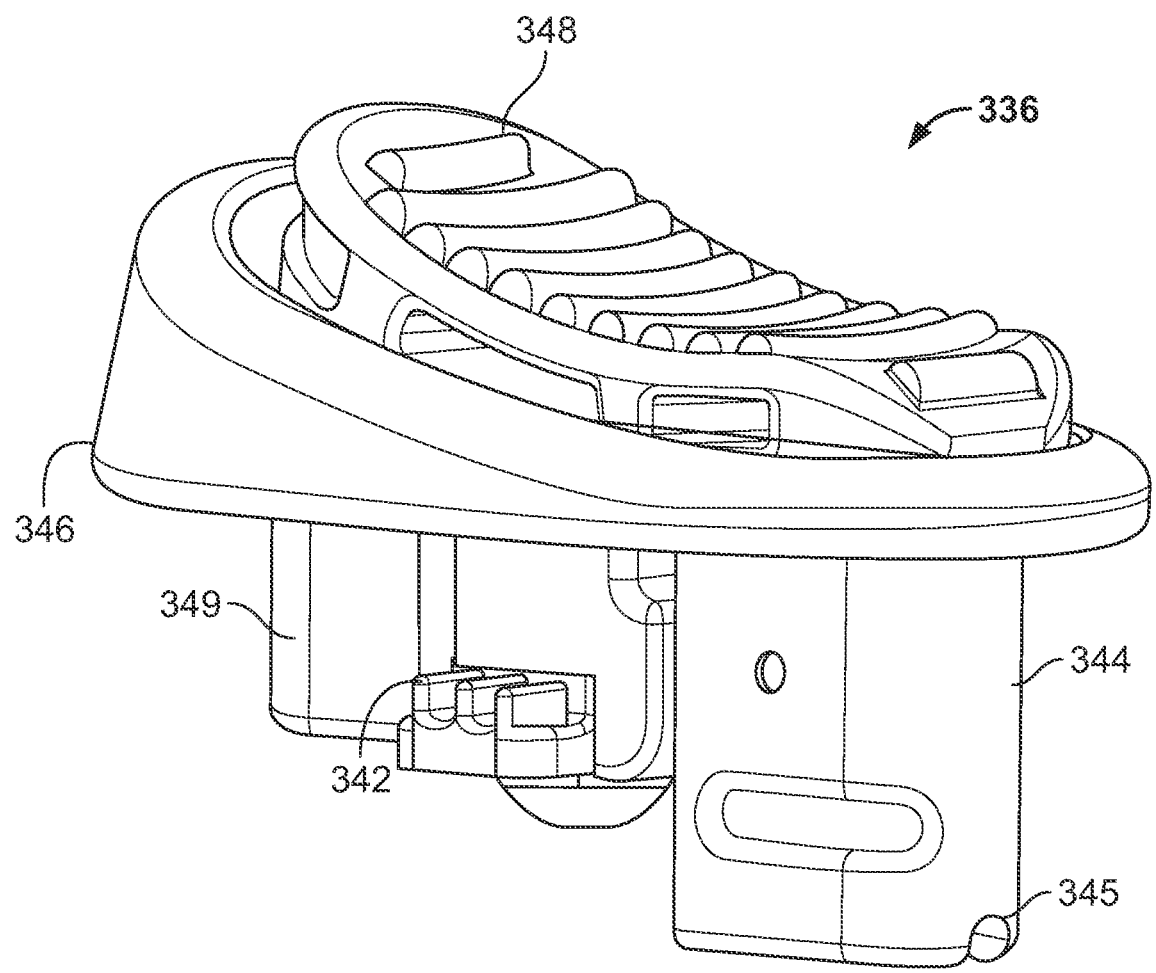
FIG. 20C shows a perspective view of a locking slider.
Figure 20D:
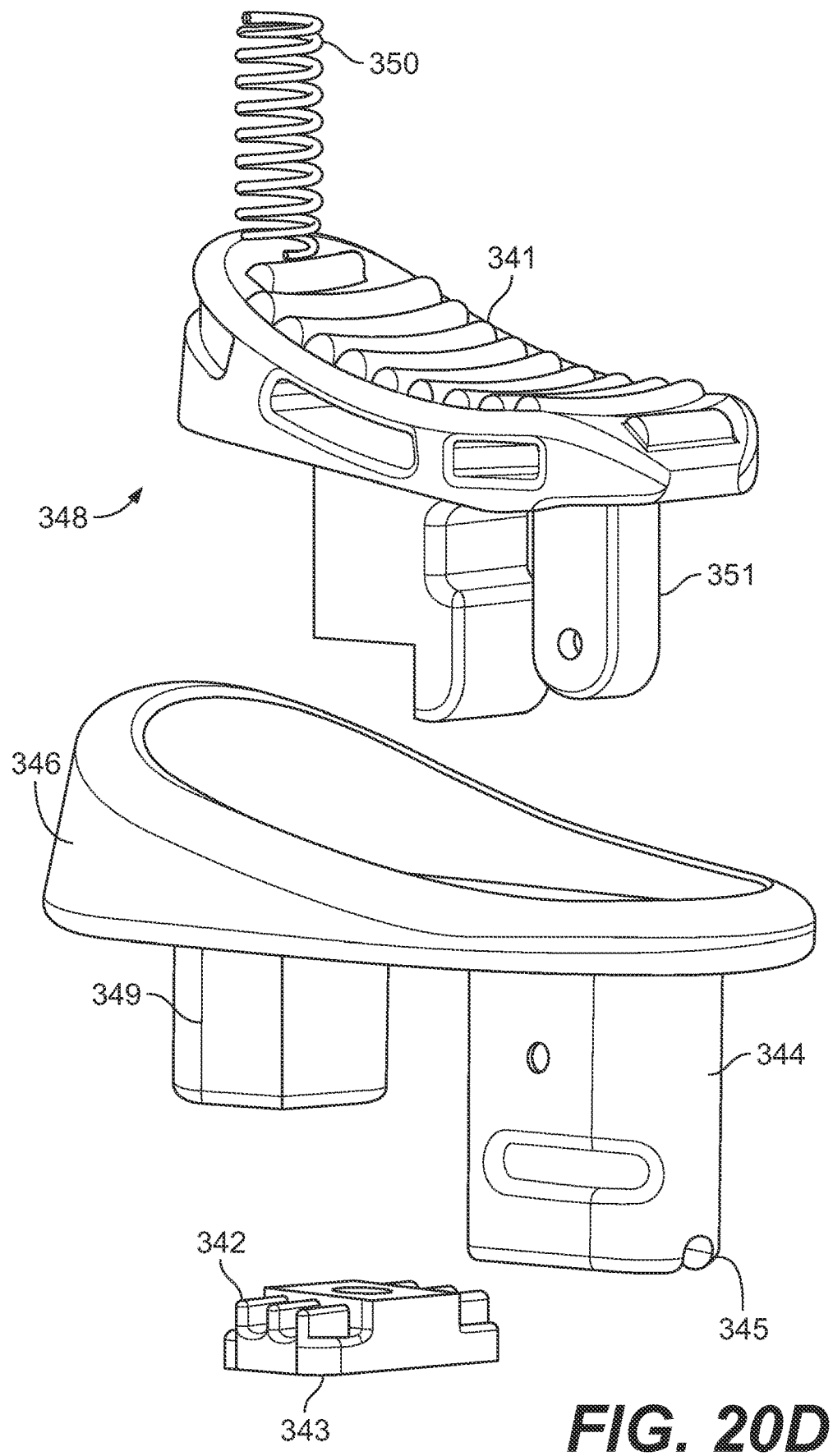
FIG. 20D shows an exploded view of the locking slider embodiment of FIG. 20C.

An additional locking slider embodiment is shown in FIGS. 20A, 20B, 20C, and 20D. FIG. 20A shows a perspective view of handle 328 including a locking slider 336 that moves proximally and distally within groove 338. FIG. 20B shows a cross sectional view of the handle 328 with activation wire 105 extending through the distal strain relief portion 339 of the handle 328 and to the to the interior components of locking slider 336. FIG. 20C shows the locking slider 336 isolated from the rest of the handle 328, such that the reader can visualize the sliding portion 346, the lock button 348, and the upward facing teeth 342 of the locking slider 336. Sliding portion 346 and lock button 348 are secured to each other at the back end by spring 350 and at the front end by post 351, as shown in FIG. 20B.

Like the locking slider 136 shown in FIG. 7C, locking slider 336 utilizes a spring 350. Spring 350 extends vertically between a back interior portion 349 of the sliding portion 346 and an underside of lock button 348. In the uncompressed state, spring 350 exerts a force on lock button 348, which presses upward facing teeth 342 into engagement with downward facing teeth 340 of an exterior casing 335 of handle 328. When the upward facing teeth 342 are engaged with downward facing teeth 340, the locking slider 336 is in the locked configuration, preventing longitudinal movement of the activation member 105 and fixing the braided assembly 102 in a fixed outer diameter. Pressing down on lock button 348 compresses spring 350, pushing teeth 342 down and away from teeth 340. With the two sets of teeth disengaged, a user can translate the locking slider 336 within the slot 338 (i.e., the locking slider 336 is in the slidable configuration, permitting longitudinal movement of the activation member 105 and allowing adjustment of the diameter of the braided assembly 102). As is evident from the exploded view of FIG. 20D, upward facing teeth 342 are provided as part of a separate component 343, which is discontinuous from lock button 348 and is coupled to lock button 348 by screw 347 (screw 347 shown in FIG. 20B).

Looking at FIGS. 20B and 20C, activation wire 105 extends through strain relief portion 339 into slot 345 on the front interior component 344 of sliding portion 346. Activation wire 105 can be secured within slot 345 by any number of means, such as, but not limited to, an adhesive. The textured gripping surface of lock button 348 slopes upward toward the proximal end of the handle, thereby maximizing friction between the user's thumb and the lock button 348. A slot cover 357 couples to front interior component 344 and includes distally and proximally extending wings 353, 355, which shield the inside of the handle 328 from the external environment as the slider 336 moves back and forth within slot 338.

Conventional thrombectomy devices utilize shape memory elements with a baseline expanded configuration. These conventional devices risk inadvertent overexpansion and damage to the vessel. Furthermore, conventional devices are often restrained by a bulky overlying sheath, which is pulled back to allow the device to self-expand.

Advantageously, using a device with a shape memory of the collapsed position reduces the risk of overexpansion and injury during self-expansion. Self-collapse also allows the device to be restrained using the low-profile activation wire system described herein. An additional advantage is the ability to expand the braided assembly to various diameters to precisely custom fit the size of the vessel. This can be especially useful if the size of the vessel is different than originally anticipated. The level of grip between the braid 9 and the surrounding thrombus can also be customized as needed by applying different levels of tension to the activation wire 105. For example, the practitioner may apply a first level of tension to deploy the braided assembly 102 to a first expanded outer diameter to contact the thrombus. If the force between the thrombus and the braid 9 is not enough to pull the thrombus toward the aspiration catheter 106, the practitioner can widen the braid 9 to a second expanded outer diameter by applying a greater second level of tension to the activation wire 105. This widened diameter provides a greater contact force between the thrombus and the braid 9, such that the thrombus can be more easily pulled toward aspiration catheter 106.

FIGS. 3A-3D show an additional embodiment of a thrombectomy device having a braided assembly 19 with multiple braided sections 111, 112. The elongated nature of this embodiment facilitates the capture and retrieval of long thrombi. As shown in FIG. 3A and FIG. 3B, each of the braided sections 111, 112 is attached to and extends around the distal region 22 of retrieval device 21. The braided assembly 19 includes multiple sliding collars 23, 25 and a fixed attachment point 27. Proximal braided section 111 is attached to and extends between the fixed attachment point 27 and the proximal slidable collar 23, where it is welded, bonded, or otherwise adhered at a central sliding attachment point 29. Distal braided section 112 is attached to and extends between the proximal slidable collar 23 and the distal slidable collar 25. In some embodiments, the braided sections are formed by constraining one larger braid with the proximal slidable collar 23. In other embodiments, each braided section is formed from a separate braid (such that each of the proximal and distal braided assemblies are separately fixedly attached to proximal slidable collar 23). In some embodiments, the slidable collars 23, 25 can be positioned distally to the fixed attachment point 27, as illustrated in FIG. 3A. In other embodiments, the slidable collars can be positioned proximally to the fixed attachment point (not shown). Though illustrated with two braided sections 111, 112, other embodiments of the braided assembly 19 could include more than two braided sections and more than two slidable collars.

FIG. 3C shows the thrombectomy device of FIGS. 3A and 3B without the braided assembly 19. Retrieval device 21 has a hypotube 131 fixedly attached to a support tube 130. A single activation wire 132 extends through hypotube 131 and support tube 130 to an exit point 134 positioned on the support tube 130. From there, it travels along the outer surface of support tube 130, running beneath proximal sliding collar 23 to attach to distal sliding collar 25. Cross sectional views shown in FIG. 3D, FIG. 3E, FIG. 3F, and FIG. 3G show the radial position of activation wire 132 with respect to hypotube 131, the support tube 130, and the guidewire tip 103 at various axial locations along the thrombectomy device shown in FIG. 3C. The activation wire 132 is utilized to control expansion of the braided assembly via connection to the distal sliding collar 25. In other embodiments, the activation wire 132 can be attached to the proximal sliding collar 23. Retrieval deviceProximal movement of the proximal slidable collar 23 or the distal slidable collar 25 by the activation wire generates a force on the other of the two slidable collars, such that the two braided sections 111, 112 are expanded (or partially expanded) in unison. As described above, the braids are formed of a shape memory material with a bias toward the collapsed configuration, so that tensioning the activation wire enables multiple levels of expansion.

Figure 4:
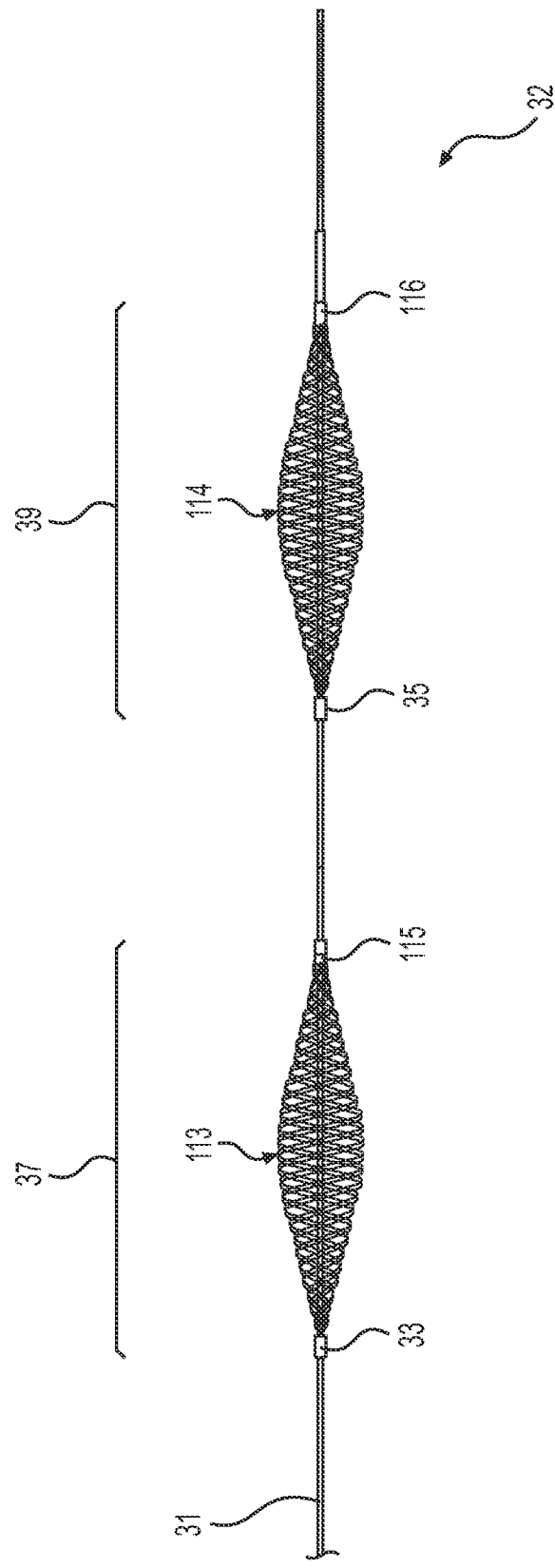
FIG. 4 shows an additional embodiment of the thrombectomy device having multiple expandable braided assemblies.

FIG. 4 shows an additional embodiment with multiple, separately expandable braided assemblies 37, 39. The braided assemblies 37, 39 are spaced from each other along the distal region 32 of retrieval device 31. The proximal braided assembly 37 includes braided section 113 that extends between a fixed attachment point 33 and a slidable collar 115. The distal braided assembly 39 includes braided section 114 that extends between a fixed attachment point 35 and a slidable collar 116. Each braided assembly is controlled by a separate activation wire, such that each braided assembly can be individually controlled. Each activation wire exits the retrieval device 31 from an exit point beneath the individual braid and attaches to the individual slidable collar (not shown). The multiple activation wires can travel through the same lumen in retrieval device 31, or they could have individual lumens. Depending upon the positioning of the slidable collars in relation to the fixed attachment points, in some embodiments, each additional activation wire can travel through the same lumen and exit the retrieval device at the same portal, or at different portals. In some embodiments, one or more activation wires can exit from the distal end of the retrieval device 31.

As with the previously described embodiments, the braids of the embodiment shown in FIG. 4 are formed of a shape memory material with a bias toward the collapsed configuration, such that tensioning the activation wire enables deployment of the braid to a range of diameters. Each braided assembly is deployable to a partially expanded configuration by placing a first level of tension in the attached activation wire, or to a fully expanded configuration by placing a second, greater level of tension into the activation wire. Thus, when multiple activation wires and braided assemblies are used, a first braided assembly can be deployed to a partially expanded state while a second braided assembly is deployed in a fully expanded state. In some scenarios, it may be advantageous for one braided assembly to be fully collapsed while another braided assembly is either partially or fully expanded. This can be advantageous, for example, when pulling a longer thrombus into the aspiration catheter 106. The proximal braided section 113 can be collapsed as it enters the aspiration catheter, prior to the distal braided section 114 which is still outside of the aspiration catheter.

In some embodiments, braids of separate braided sections or separate braided assemblies can have different properties, such as different maximum expanded diameters, different wire sizes, different wire densities, different numbers of wires, etc. These properties can vary depending upon the positioning of the braided section or the braided assembly along the retrieval device. For example, the distal braided section or braided assembly might have a larger expanded diameter to better pull back against the thrombus, while the proximal braided section(s) or braided assembly(s) might be less dense and stronger to better engage the middle of the thrombus.

FIGS. 5A-5C show an embodiment of the thrombectomy device that enables use with a guidewire, such that a practitioner can remove and reinsert the device to the same anatomic position multiple times (for example, to clean the device during the procedure). FIG. 5A shows aspiration catheter 127, retrieval device 121, guidewire tubing 118, braided assembly 123 (in the collapsed configuration), and guidewire 45. Guidewire tubing 118 is positioned around the distal region 61 of retrieval device 121. The guidewire tubing 118 is shorter than the retrieval device 121 in the longitudinal direction, such that the guidewire 45 leaves the guidewire tubing 118 at the proximal guidewire exit 117 and extends alongside retrieval device in a proximal direction. FIG. 5B shows the embodiment of FIG. 5A with the braided assembly 123 in an expanded state. As shown in the cross section of FIG. 5C taken at line B-B of FIG. 5B, guidewire 45 extends through the first lumen 124 of the guidewire tubing 118. The guidewire 45 exits guidewire tubing 118 at distal guidewire exit 47. The guidewire tubing 118 can include a distal atraumatic tip 120. The guidewire tubing 118 can be formed, for example, of a polymer material. Retrieval device 121, including activation wire 125, extends through a second lumen 126 of the guidewire tubing 118. As described above, the activation wire 125 is connected on the proximal end to a tensioning element, extends through retrieval device 121 to an exit point, leaves the retrieval device 121 at the exit point (beneath the braid), and attaches at its distal end to the slidable distal collar 122 on the braided assembly 123. The exit point can be, for example, a tunnel through the sidewalls of the retrieval device 121 and the guidewire tubing 118 (i.e., a tunnel formed by a portal in the sidewall of the retrieval device 121 that is aligned/coaxial with a portal in the sidewall of the guidewire tubing 118). In use, the guidewire tubing 118 and the retrieval device 121 are introduced together over the previously placed vascular guidewire 45. Because the guidewire 45 is retained within the guidewire tubing 118, it is pulled at least partially to the side within the lumen of aspiration catheter 127 and can move without interfering with activation wire 125. The guidewire tubing 118 and the retrieval device 121 keep the activation wire 125 and the guidewire 45 moving in an axial direction, independently from one another, using a low-profile and low-friction design. Once in position, the braided assembly 123 is expanded and the proximal end of the aspiration catheter 127 is connected to a vacuum source. The braided assembly 123 is expanded and then retracted back toward the aspiration catheter 127, pulling the clot with it and breaking it into small pieces.

Figure 6A:
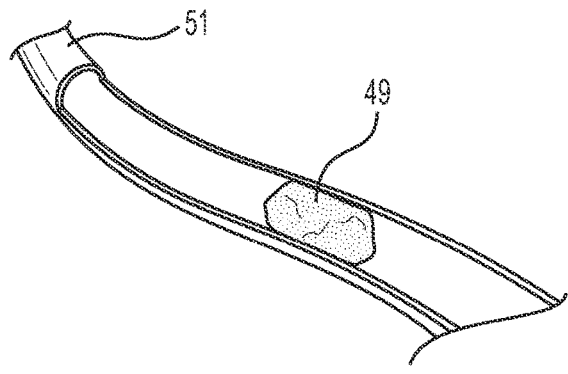
FIGS. 6A-6F show an example method of using a thrombectomy device.

Methods of performing thrombectomy procedures are also disclosed herein. An example method is illustrated in FIGS. 6A-6F. FIG. 6A illustrates thrombus 49 occluding vessel 51. Distal end of aspiration catheter 53 is advanced through the vasculature to an area proximal to the thrombus 49, as shown in FIG. 6B. The distal end of retrieval device 55 carrying braided assembly 57 is advanced out the distal end of the aspiration catheter 53 and through thrombus 49, such that the braided assembly 57 is distal to thrombus 49, as shown in FIG. 6C. The practitioner then places tension in the activation wire housed inside the retrieval device 55, thereby moving the activation wire longitudinally within the lumen of the retrieval device and moving the slidable collar of the braided assembly longitudinally over the exterior surface of the retrieval device. Movement of the slidable collar via the activation wire causes braided assembly 57 to expand to the diameter of the practitioner's choosing. Should the practitioner wish to alter the level of expansion during the procedure (i.e., change the maximum diameter d of the braided assembly 57), this is made possible by altering the level of tension in the activation wire, which again moves the activation wire within the retrieval device and moves the slidable collar, as described above. Advantageously, the distal end of the retrieval device 55 maintains a stationary position as the braided assembly is expanded to the optimal diameter. Maintaining a constant position of the distal end of retrieval device 55 is advantageous because sliding proximal/distal movement of the distal end within the vessel can result in vessel damage or perforation.

Figure 6D:
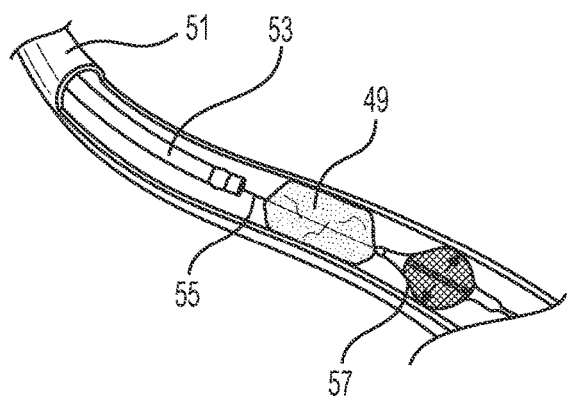
Figure 6B:
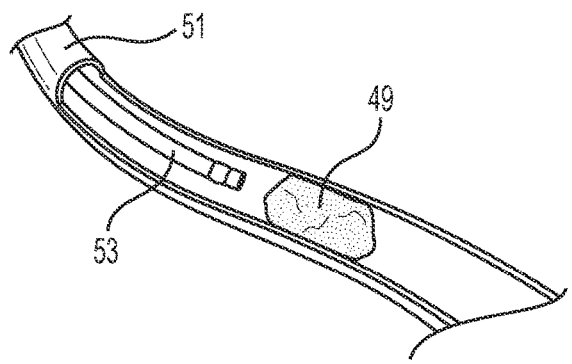
Figure 6E:
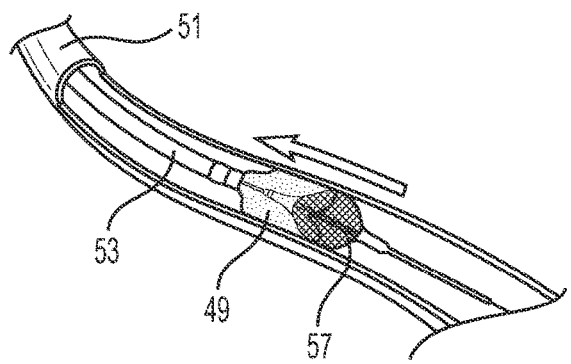
Figure 6C:
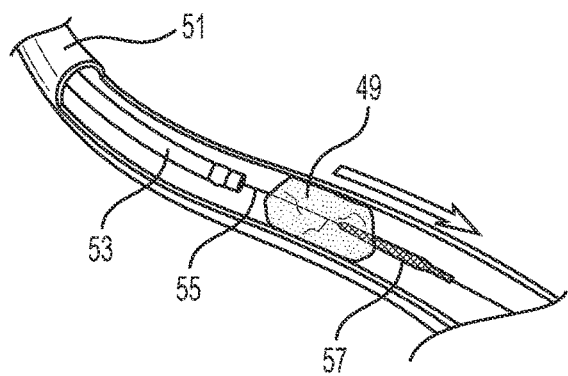
Figure 6F:
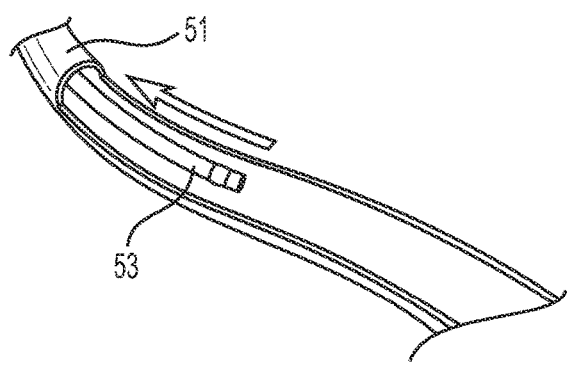

FIG. 6D shows the braided assembly 57 in an expanded configuration, sized to fit the vessel 51. The practitioner then pulls the retrieval device 55 proximally and contacts the thrombus 49 with the braided assembly 57, as shown in FIG. 6E. The thrombus 49 and braided assembly 57 are pulled proximally toward aspiration catheter 53. The aspiration catheter 53 can be connected to an external vacuum source (not shown), which enables the aspiration of the thrombus 49 into the distal end of the aspiration catheter 53. The aspiration catheter 53 is then retracted proximally, as illustrated in FIG. 6F, and removed from the body.

The ability to open the braided assembly to a range of different diameters is useful to thrombectomy procedures for multiple reasons and in multiple scenarios. The ability to custom fit the braid to a particular vessel during the procedure is preferable over introducing a braid that expands to a predetermined size, then discovering mid-procedure that it is either too small to grip the thrombus or that it is too large and has damaged the vessel. As another exemplary advantage, the level of grip between the braid and the thrombus can be optimized mid-procedure. For example, the practitioner may apply a first level of tension to the activation wire to deploy the braided assembly to a first expanded outer diameter to contact the thrombus. If the force between the thrombus and the braid is not sufficient to pull the thrombus toward the aspiration catheter, the practitioner can widen the braid to a second expanded outer diameter by applying a greater second level of tension to the activation wire. This widened diameter increases the contact force between the thrombus and the braid, such that the thrombus is more easily pulled toward aspiration catheter.

The methods can also be performed using a guidewire. For example, the guidewire can be positioned distal to the thrombus prior to advancing the distal end of the retrieval device. The retrieval device extends at least partially through a lumen of the guidewire tubing, such as in the embodiment of FIGS. 5A-5C. Together, the retrieval device and guidewire tubing are advanced over the guidewire and toward the thrombus. The guidewire extends through a separate lumen of the guidewire tubing than the retrieval device and activation wire. Once positioned, the activation wire is moved longitudinally within the retrieval device to expand the braided assembly.

Long thrombi can be addressed using braided assemblies with multiple braided sections such as the embodiment shown in FIG. 3. Movement of the slidable collar results in expansion of more than one of the braided sections, resulting in a relatively long braided assembly. In some embodiments a device with multiple, separately expandable braided assemblies, such as the one shown in FIG. 4, can be used to treat long thrombi. With separately expandable braided assemblies, as the thrombus is drawn proximally closer to the distal end of the aspiration catheter, the proximally positioned braided assembly collapses from a first expanded outer diameter to the collapsed diameter (or to a narrower second expanded outer diameter). The distally positioned braided assembly maintains an expanded outer diameter that is greater than the outer diameter of the proximally positioned braided assembly until it too is pulled into the aspiration catheter.

Various implementations of the thrombectomy device and its corresponding components are formed from one or more biocompatible materials, such as cobalt chromium, titanium and titanium alloys, stainless steel, nitinol, platinum, gold, or other metals, as well as ceramics or polymers. In addition, in some implementations, the thrombectomy device or portions thereof includes a coated material.

Figure 8:
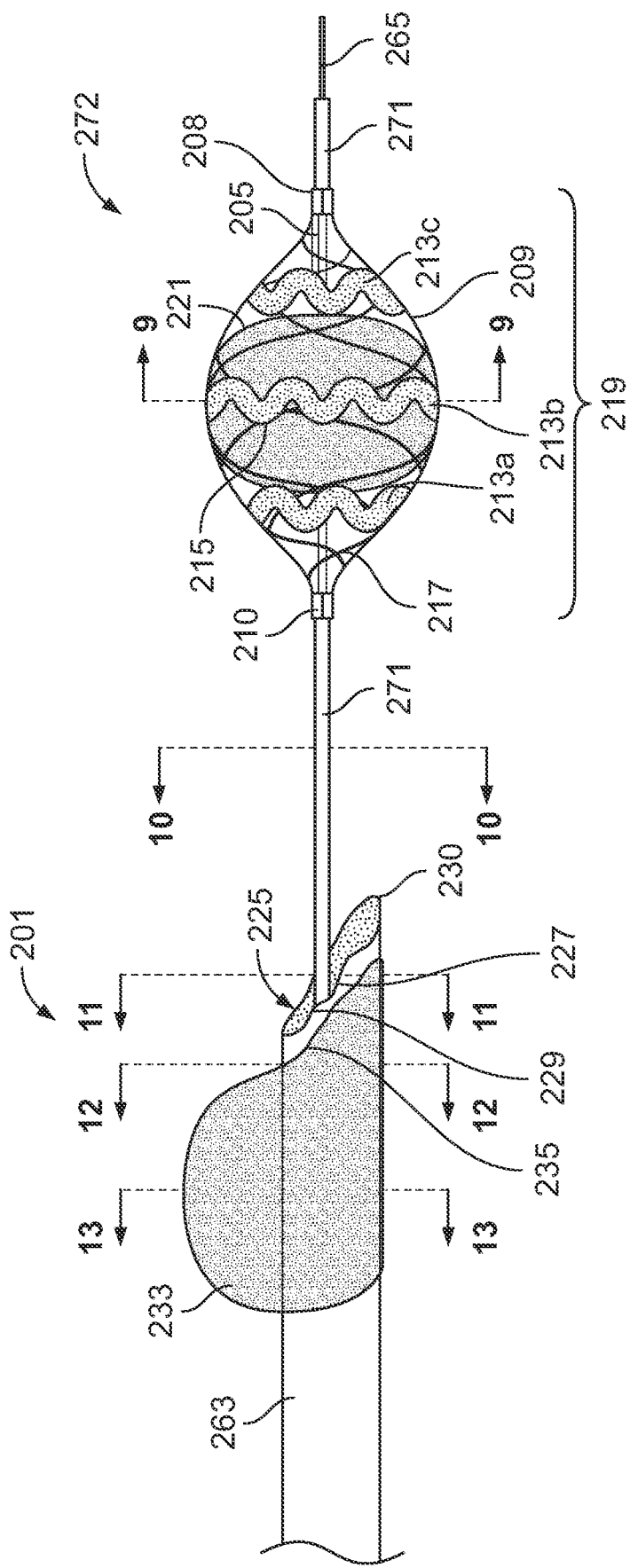
FIG. 8 shows an embodiment of a thrombectomy device.

FIG. 8 shows another embodiment of a thrombectomy device 201. Thrombectomy device 201 includes aspiration catheter 263 and retrieval device 271 extending through the aspiration catheter 263. Similar to the embodiments described above, distal region 272 of the retrieval device 271 is coupled to a braided assembly 219. The retrieval device 271 has an interior lumen 207 (as shown in the cross-sections of FIGS. 9-13). A guidewire 265 and an activation wire 205 (or activation member 205) extend through the lumen 207 of the retrieval device 271. The activation wire 205 exits from the sidewall of retrieval device 271 to attach to a slidable collar 208 of the braided assembly 219. The slidable collar 208 encircles the retrieval device 271. Braid 209 of the braided assembly 219 is coupled to the slidable collar 208 at one end, and to the retrieval device 271 at the other end via a fixed attachment point 210. Activation wire 205 pulls on slidable collar 208, providing an expansion force to overcome the shape memory bias of the braid 209 (the shape memory bias is toward the collapsed state). Thus, the braided assembly 219 can be expanded to a range of outer diameters by varying the level of tension in the activation wire 205 and sliding the slidable collar 208 closer or farther from fixed attachment point 210.

In contrast to the previously described embodiments, the braided assembly 219 of FIG. 8 also includes circumferentially extending, oscillating rings 213 encircling braid 209. Rings 213 can be attached to the braid 209 by, for example, spot welding, weaving the wires 217, 218 through the rings 213, or braiding the rings 213 in with the wires 217, 218. Rings 213 expand and collapse with the underlying braid 209. The flat outer surfaces of rings 213 that encircle braid 209 are intended to come into contact with the thrombus. One or more rings 213 can be provided along the length of the braid 209. As shown in FIG. 8, the oscillating pattern of a ring 213 creates apices 215 that point in a longitudinal direction. As shown in the cross section of FIG. 9, a ring 213 extends radially outwardly a short distance from the braid 209.

Though three rings 213a, 213b, and 213c are shown in FIG. 8, multiple rings (i.e., 1, 2, 4, 5, or more rings) could be positioned at various longitudinal locations along braid 209. For example, one ring 213a be positioned longitudinally adjacent to and rotated slightly as compared to the a second ring 213b, such that the apices 215 of the second ring 213b occur at different circumferential locations than apices 215 of the first ring 213a. In some embodiments, only part of a ring may be utilized (i.e., an arc of a ring extending only partially around the circumference of the braid 209).

Figure 9:
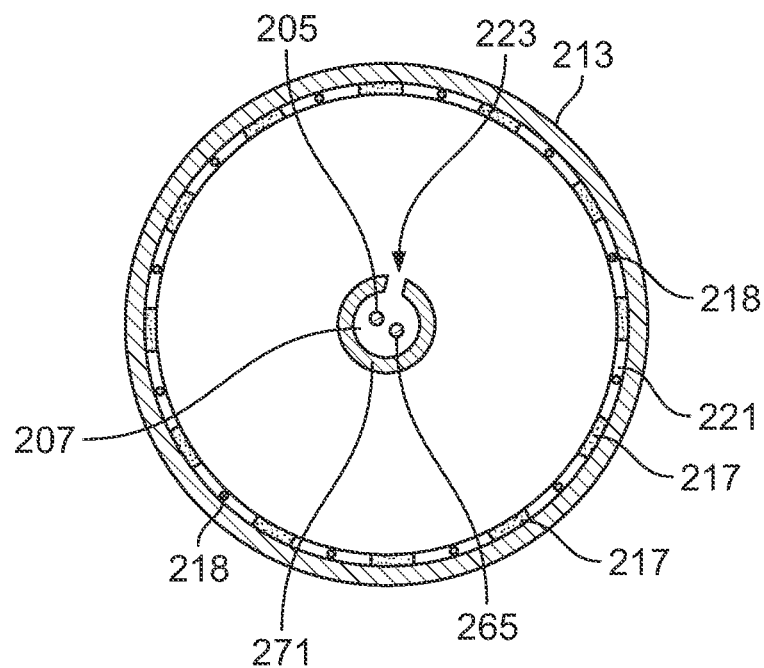
FIG. 9 shows a cross section of the thrombectomy device of FIG. 8, taken at line 9-9.

Like rings 213, the smaller wires 217 of braid 209 may be flattened. For example, the outer and inner surfaces of the smaller flat wires 217 can have flattened, smooth surfaces. Together, the flattened shapes of the rings 213 and flat wires 217 harmlessly shave off pieces of the thrombus as the expanded braided assembly 219 is pulled proximally toward the aspiration catheter 263 by retrieval device 271, promoting maceration of the thrombus to a size that can be easily aspirated into catheter 263. The flattened rings 213 and flat wires 217 are also helpful for clearing clogs within aspiration catheter 263. As shown in FIG. 9, the braid 209 can also incorporate small, rounded wires 218, which are circular or oval in cross section. The ratio of round to flat wires can be optimized for the particular technique. The ring 213 and wires 217, 218 can be made of stainless steel, nitinol, a shape memory metal, or a shape memory polymer.

Furthermore, an expander 221 can be coupled to retrieval device 271 for exerting an outward expansion force upon the braided assembly 219. Expander 221 is coupled to the outer surface of the retrieval device 271 beneath the braid 209 of the braided assembly 219. The expander 221 can maximize or optimize the apposition force that braided wires 217, 218 and ring(s) 213 apply to the thrombus. In some embodiments, the expander 221 can be a balloon, or a balloon disc. However, the disclosure is not limited to the use of a balloon as the expander 221. Any expandable and collapsible device which can exert an outward expansion force upon the braided assembly 219 could serve as expander 271. The expander 221 is coupled to the retrieval device 271 at proximal and distal fixation points. When expander 221 is a balloon, the retrieval device 271 can include an inflation port 223 in fluid communication with expander 221. The inflation port 223 enables inflation fluid to be released into the expander 221 (see FIG. 9). Alternatively, the expander may be in fluid communication with a separate expander catheter (e.g., a balloon catheter). When expander 221 is a balloon, the balloon can be formed of polyurethanes, PEBAX, and/or nylon, for example. The balloon can be compliant, rigid, or a combination thereof to tailor the inflation pressure and to suit the vessel size and the particular procedure.

Expander 221 can be used in conjunction with the braided assembly 219 described above (i.e., an activation wire 205 attached to a slidable collar 208 that slides longitudinally to expand and collapse a braid 209, the braid 209 having a bias toward the collapsed position). Alternatively, the expander 221 can be used in conjunction with a self-expanding braided assembly. The expanded diameter of expander 221 can be chosen to match the maximum expanded diameter of braid 209.

While the embodiment of FIG. 8 shows the distal end 272 of retrieval device 271 having both an oscillating ring 213 and an expander 221, in some embodiments one may be incorporated without the other. For example, an expander 221 can be attached to a retrieval device that does not include an oscillating ring 213. In other embodiments, a ring 213 can be incorporated around a braid 209, without an underlying expander 221.

Notably, various features of the disclosed thrombectomy devices help to prevent inversion of the braid 209 during a thrombectomy procedure. For example, expander 221 can pop the braid 209 back out if it is inverted, or expander 221 can prevent the inversion of the braid 209 altogether. Rings 213 can also prevent inversion by rigidifying the braid 209, especially when placed adjacent to the proximal and distal ends of the braid 209 (like 213a and 213c). Rings 213 need not oscillate to perform this function. In some embodiments, certain rings may oscillate and provide apices 215 to assist with scraping, whereas rings adjacent to proximal or distal ends of the braid perform reinforcing functions and do not oscillate. Finally, the design of the braid can be optimized to limit inversion. Greater numbers of thicker wires generally lead to fewer inversion incidents, but this advantage must be balanced with the need for braid flexibility. The length of the braid 209 also plays a role in its resistance to inversion. Shorter braids being more resistant to inversion, but this advantage must also be balanced with the benefit of longer braids contacting more thrombus.

Figure 14:
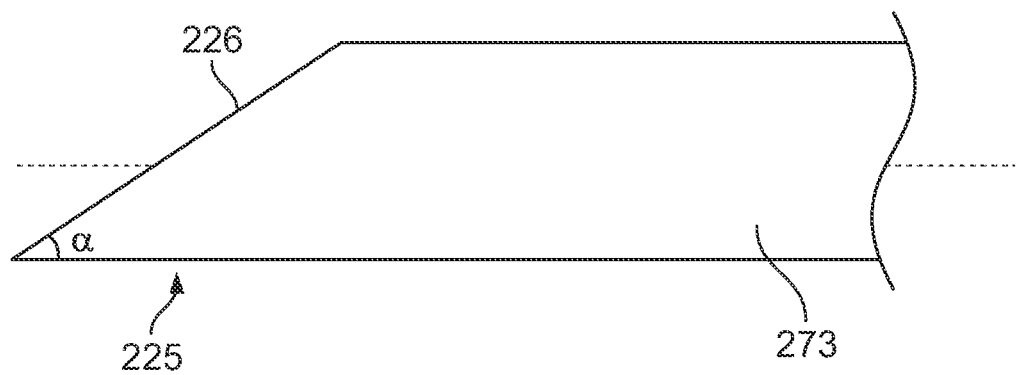
FIG. 14 shows an embodiment of an aspiration catheter.
Figure 15:
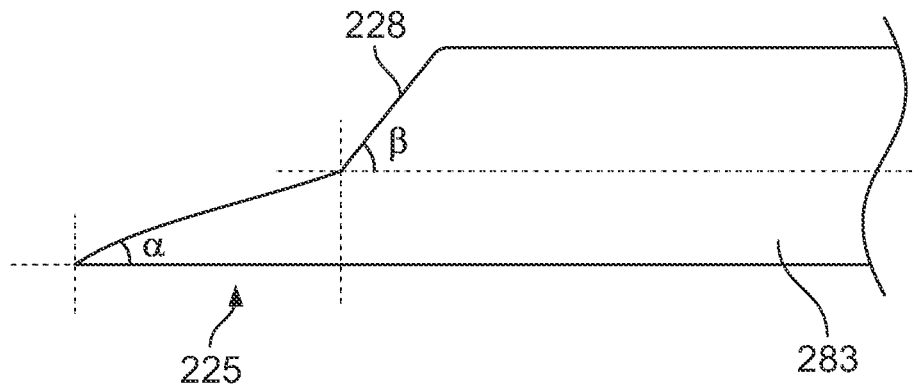
FIG. 15 shows an embodiment of an aspiration catheter.

The aspiration catheter 263 shown in FIG. 8 has a beveled distal end 225 with an uneven edge 227. The bevel of the distal end 225 gives the distal end 225 the shape of a scoop. The bevel also increases the aspiration area of the distal end 225 as compared to conventional aspiration catheters, which have distal ends that create a plane lying perpendicular to the longitudinal axis of the catheter. This increase in aspiration area at distal end 225 enables entry of larger clots. The catheter is beveled by angle α, as shown in the aspiration catheter 273 of FIG. 14. The angle α of the edge 226 of the beveled distal end 225 can be from about 15 degrees to about 75 degrees, or, in some examples, from about 30 degrees to about 60 degrees (including about 30 degrees, about 35 degrees, about 40 degrees, about 45 degrees, about 50 degrees, about 55 degrees, and about 60 degrees). The angle of the edge 226 is the angle formed between the edge at a given point and an imaginary line originating at that same point and extending longitudinally along the surface of the catheter (parallel to the longitudinal axis). In some embodiments, such as aspiration catheter 283 shown in FIG. 15, the angle can increase travelling proximally along the edge 228. For example, the bevel may take an angle β about halfway up the edge 228, where β is greater than α. The increase in angle may occur abruptly, as shown in FIG. 15, or the angle may gradually increase travelling proximally along the edge 228.

Figure 16:
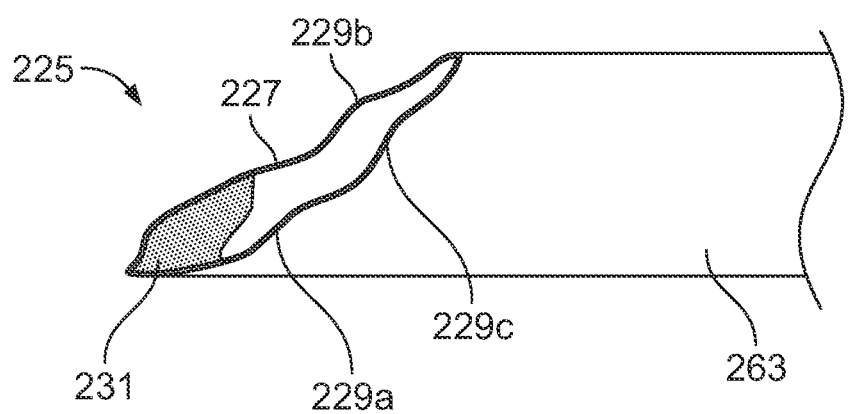
FIG. 16 shows an embodiment of an aspiration catheter.
Figure 17:
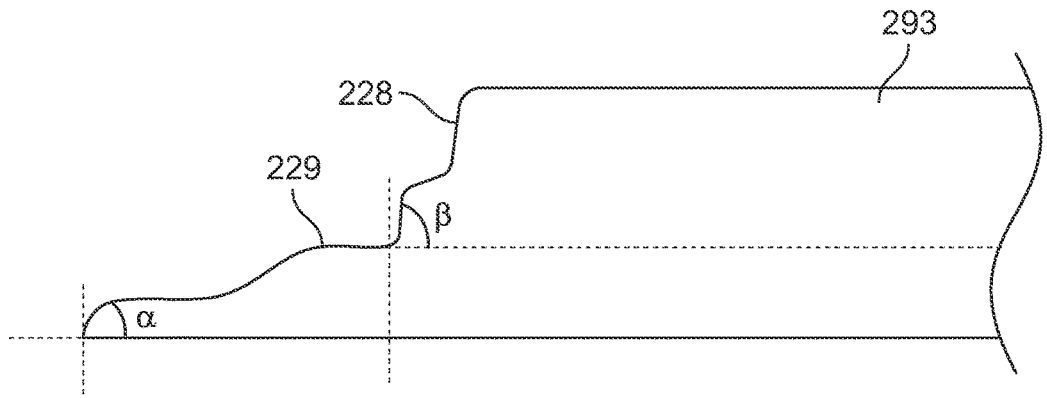
FIG. 17 shows an embodiment of an aspiration catheter.

The distal end 225 of the aspiration catheters disclosed herein can have undulations 229 that create a scalloped, uneven edge 227. The uneven edge 227 can be used to help dislodge a stubborn thrombus—the contact force between the catheter 263 and the thrombus is concentrated in the distal-most edges of the undulations 229. This contact force can help to break off pieces of the thrombus. Another embodiment of an aspiration catheter with an uneven edge is shown in FIG. 16. As seen in FIG. 16, undulations 229*a*, 229*b* and 229*c* are gently sloped, with a large radius of curvature. However, in other embodiments, undulations 229 can be tightly packed and/or have a smaller radius of curvature to create more abrupt protrusions. This may be helpful in certain anatomical settings, or when the thrombus is expected to be difficult to remove. The number and positioning of the undulations 229 can vary. Undulations 229 may be positioned in a predictable pattern, or they may be positioned sporadically along edge 227. Some embodiments, such as aspiration catheter 273, can have a smooth distal edge 226, with no undulations at all (see FIG. 14). Some embodiments, such as aspiration catheter 293 in FIG. 17, can have undulations 229 and a distal edge 228 with an angle that increases travelling proximally along the catheter 293.

As shown in FIG. 16, the aspiration catheters disclosed herein can include a distal tip 231 formed of a distinct material than the more proximal regions of the aspiration catheter. For example, the distal tip 231 can be a polymer infused with a radiopaque powder. Radiopacity enables the aspiration catheter to be visible to the practitioner during the procedure using medical imaging techniques. In some embodiments, the distal tip 231 is coupled to catheter 263 via epoxy or reflow techniques.

As shown in FIG. 8, aspiration catheter 263 also includes a blocking element 233. The blocking element 233 extends circumferentially around the aspiration catheter 263. It can be expanded at the procedure site to limit or block proximal blood flow. The blocking element 233 can be a balloon, for example. When a balloon utilized as the blocking element 233, an inflation lumen can extend through the sidewall of aspiration catheter 263 with an inflation port in fluid communication with the blocking element 233 to enable inflation fluid to enter the blocking element 233. In other embodiments where the blocking element 233 is a balloon, a separate balloon catheter can be routed through the central lumen of aspiration catheter 263 and be placed in fluid communication with the blocking element 233 via an inflation port through the side of aspiration catheter 263. Where a balloon is used, the balloon can be compliant, rigid, or a combination thereof to suit the vessel size and the particular procedure. However, the disclosure is not limited to the use of a balloon as the blocking element 233. Any expandable and collapsible device which can at least partially block proximal blood flow can serve as a blocking element.

In some embodiments, blocking element 233 can be coupled to an outer surface of the aspiration catheter 263. The blocking element 233 can be asymmetrically positioned around aspiration catheter 263 in order to push one side of aspiration catheter 263 up against the vascular wall. In the embodiment shown, the positioning of blocking element 233 would push the distal tip 230 up against the vascular wall. The blocking element 233 is attached to the aspiration catheter 263 along a fixation line 235 that approximates the angle of the beveled distal edge 227. The fixation line 235 is positioned adjacent to the distal edge 227. These features—the asymmetric positioning of blocking element 233, the beveled fixation line 235, and the positioning of the blocking element 233 adjacent the distal edge 277—reduce blood turbulence and maximize aspiration efficiency into distal end 225 of aspiration catheter 263. These features also reduce the chance that pieces of thrombus escape capture and cause micro-embolisms after the withdrawal of the thrombectomy device 201.

Figure 10:
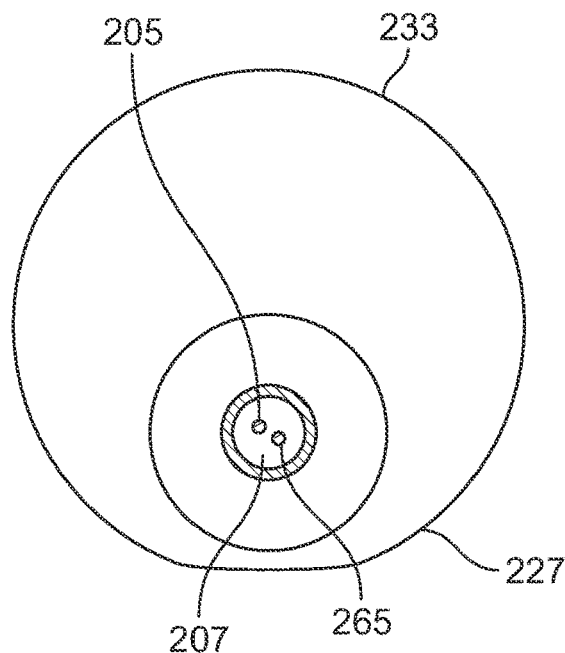
FIG. 10 shows a cross section of the thrombectomy device of FIG. 8, taken at line 10-10.
Figure 11:
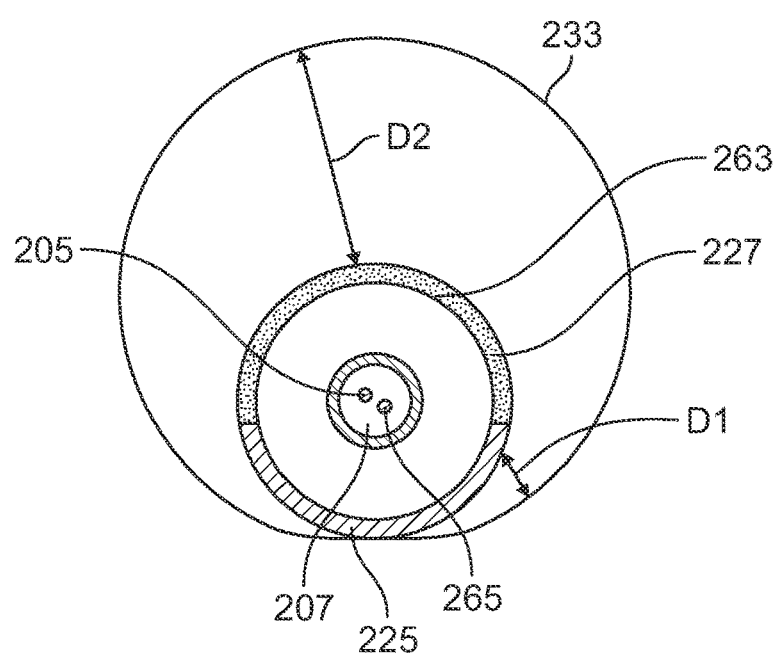
FIG. 11 shows a cross section of the thrombectomy device of FIG. 8, taken at line 11-11.
Figure 12:
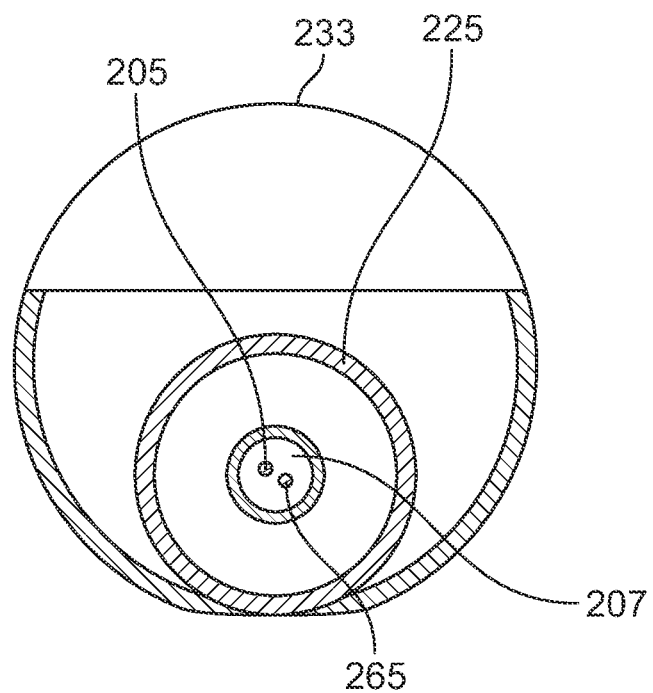
FIG. 12 shows a cross section of the thrombectomy device of FIG. 8, taken at line 12-12.
Figure 13:
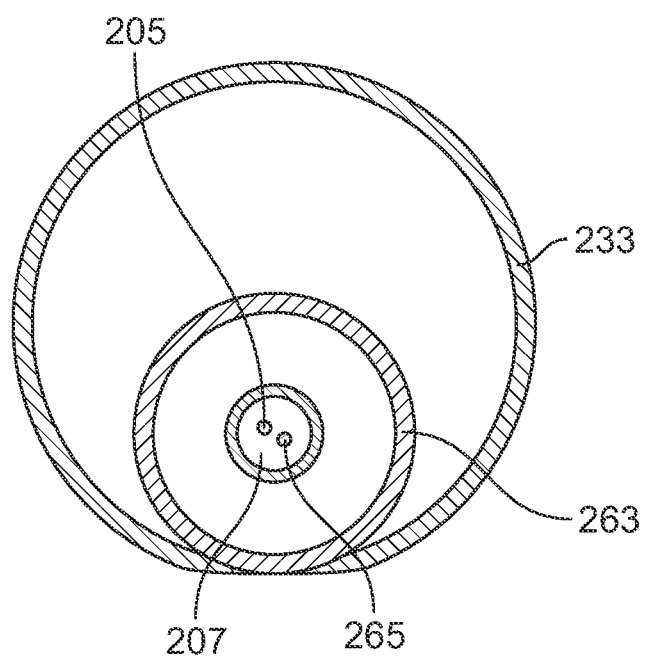
FIG. 13 shows a cross section of the thrombectomy device of FIG. 8, taken at line 13-13.

Different views of the asymmetric positioning of blocking element 233 are shown in FIGS. 10-13. FIG. 10 is a cross section taken distal to the distal tip 230 of aspiration catheter 263 and looking toward aspiration catheter 263. FIG. 11 is a cross section taken partway down the bevel of distal end 225. FIG. 12 is a cross section taken past the beveled distal end 225 and partway down blocking element 233, at the top of fixation line 235. FIG. 13 is a cross-section taken through the most expanded portion of the blocking element 233. As shown in FIG. 11, the asymmetric positioning means that blocking element 233 extends a distance D1 radially outwardly from a first side of the aspiration catheter 263 and a distance D2 radially outwardly from a second side of the catheter 263, and distance D2 is greater than distance D1.

Figure 18:
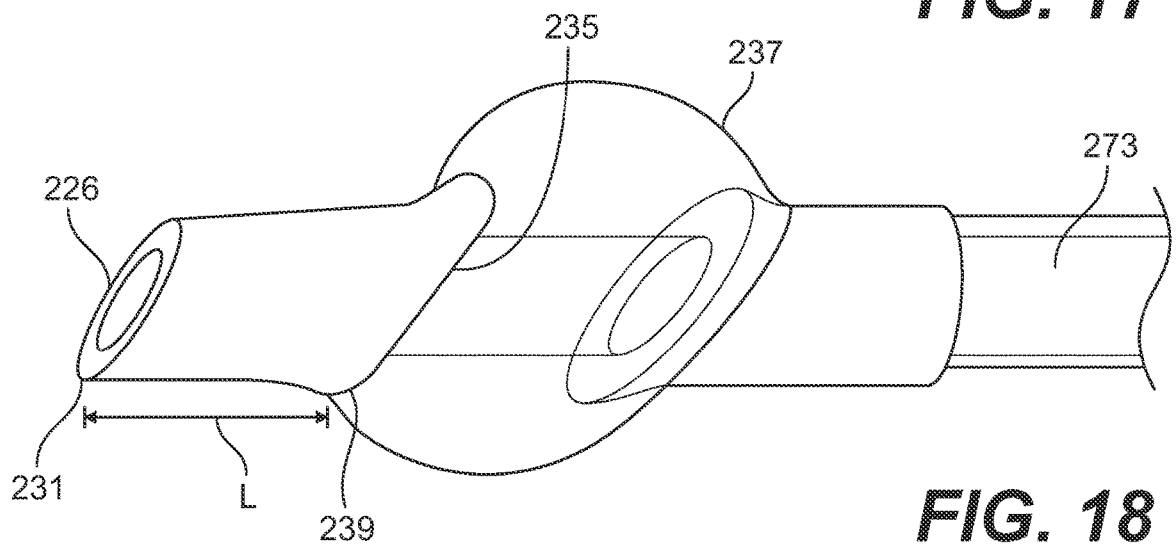
FIG. 18 shows an embodiment of an aspiration catheter including a blocking element.
Figure 19:
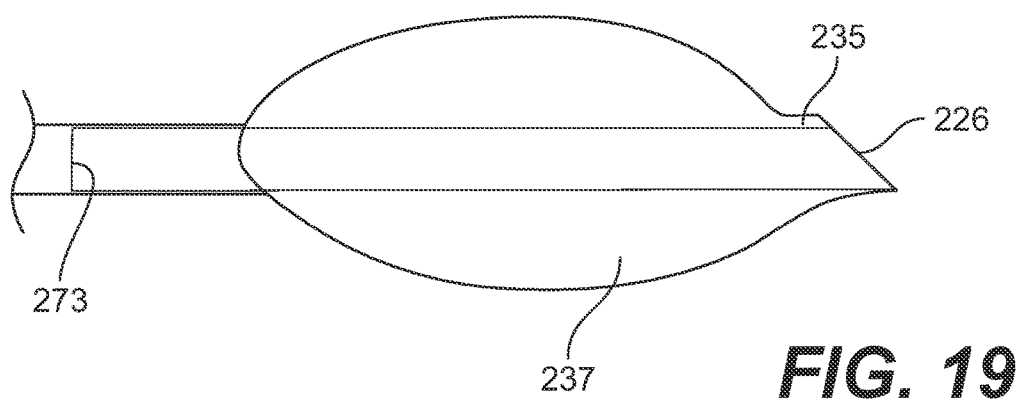
FIG. 19 shows an embodiment of an aspiration catheter including a blocking element.

However, asymmetric positioning of the blocking element is optional. In some embodiments, as shown in FIG. 18 and FIG. 19, blocking element 237 is concentric with aspiration catheter 273. Furthermore, the length L between the distal edge 226 and the fixation line 235 of the balloon can vary (greater in FIG. 18 than in FIG. 19). In some embodiments, the distal most tip of fixation line 235 can be from about 0 millimeters to about 10 millimeters from the distal tip 231 of the catheter.

With exemplary thrombectomy device 201 being thusly disclosed, a greater appreciation of the construction and benefits may be gained from the following discussion of methods for performing thrombectomy procedures. It is to be noted that this discussion is provided for illustrative purposes only. For illustration, reference will be made to the parts and features of the embodiment of FIG. 8. It is to be understood that any of the aforementioned embodiments can be used in the methods of performing thrombectomy procedures.

The methods of performing thrombectomy procedures can include advancing a guidewire 265 to a position distal to the thrombus, then advancing a beveled distal end 225 of an aspiration catheter 263 through the vasculature to an area proximal to a thrombus. The distal end of a retrieval device 271 is advanced out of the beveled distal end of the aspiration catheter 263 and to a position distal to the thrombus. In some implementations, the retrieval device 271 is advanced over the guidewire 265. The retrieval device 271 carries at least one braided assembly 219. An activation wire 205 that attaches to the braided assembly 219 is placed under a first level of tension, which deploys the braided assembly to a first expanded outer diameter. The activation wire 205 is then placed under a second level of tension, which deploys the braided assembly 219 to a second expanded outer diameter. The braided assembly 219 contacts the thrombus and pulls the thrombus proximally toward the beveled distal end 225 of the aspiration catheter 263. The thrombus is aspirated into the distal end 225 of the aspiration catheter 263. The braided assembly 219 is collapsed and retrieval device 271 is withdrawn into the aspiration catheter 263. If an oscillating ring 213 is included, it is folded and collapsed with the braided assembly 219. Blood flow is restored and the aspiration catheter 263 is removed from the subject.

In some implementations of the method, the braided assembly 219 returns to the thrombus to pull more thrombus toward the aspiration catheter 263 (similar to the methods described above with respect to FIGS. 6A-6D). Back and forth movement of the braided assembly 219 within the vessel is achieved by pulling or pushing the handle 128, which is coupled to the retrieval device 271. This pushing and pulling is facilitated by a lubricious coating over a proximal region of the retrieval device, which assists in sliding the retrieval device through the seal(s) of the aspiration catheter hub 202. A reinforced proximal segment 109 assists in pushing and pulling the retrieval device 3 through a tightly sealed catheter hub 202, as described above with respect to FIG. 2.

In some implementations of the methods of use, the beveled distal end 225 of the aspiration catheter 263 is advanced within the vasculature right up to the thrombus. The distal end 225 of the aspiration catheter 263 contacts the thrombus. In some examples, the distal end 225 can be pushed, rotated and/or scraped against the thrombus to help dislodge it. In some implementations, undulations 229 of an uneven distal edge 227 can concentrate the forces exerted against the thrombus to further assist in dislodging it. The vacuum of the aspiration catheter 263 can be activated during the contact between the distal end 225 and the thrombus.

Some implementations of the methods of use include least partially blocking fluid flow within the vasculature. For example, a blocking element 233 (such as a balloon) can be expanded (or inflated) from an outer surface of the aspiration catheter 263 to block blood flow within the vasculature. In some example methods, the blocking element 233 expands asymmetrically. This asymmetric expansion can press an outer surface of the aspiration catheter 263 up against a side of the vasculature. For example, in the example embodiment of FIG. 8, the asymmetric expansion would push the distal tip 230 of the aspiration catheter 263 up against the side of the vasculature. In some example methods, one vessel of a bifurcation or trifurcation is selectively blocked.

In some implementations of the method of use, placing tension in the activation wire 205 moves a slidable collar 208 longitudinally over an exterior surface of the retrieval device 271 in order to deploy the braided assembly 219 to the first and second expanded outer diameters. The braided assembly 219 is expanded to the first expanded outer diameter by placing a first level of tension within the activation wire 205. Then, a greater, second level of tension is placed on the activation wire 205 to open the braided assembly 219 to the wider second expanded outer diameter in order to more firmly contact the thrombus with the braid 209.

Some implementations of the methods include locking the braided assembly 102 (or braided assembly 219) in a fixed outer diameter. With the outer diameter of the braided assembly 102 locked in place, the practitioner can focus on pulling the handle proximally to retract the fixed braided assembly 102 against the thrombus inside the vessel, thereby scraping thrombus toward the aspiration catheter. In some implementations, the braided assembly 102 can be locked in a fixed outer diameter by using a locking slider 136 (or locking slider 336, for example) to prevent longitudinal movement of the activation member 105 (or activation member 205). The locking slider 136 can include a set of teeth 142 that engages with a separate set of teeth 140 on the handle 128. Teeth 142 are engaged with teeth 140 to lock the slider 136 and braided assembly 102, and disengaged to unlock the slider 136 and braided assembly 102. The disengagement of the teeth can be achieved by compressing a lock button 148 of locking slider 136, thereby compressing a spring 150 that otherwise pushes the teeth 140 into engagement with teeth 142.

In some implementations of the methods of use, an expander 221 is deployed beneath the braided assembly 219. For example, an expander 221 can be a balloon that is inflated against the inner surface of the braid 209 of the braided assembly 219. The expander 221 exerts an outward expansion force on the braid 209 to maximize contact between the braid 209 and the thrombus, thereby assisting with the removal of the thrombus. That is, the expander 221 can push the wires 217 of the braid 209 slightly into the thrombus to increase the gripping force when the thrombus is pulled toward the aspiration catheter 263. Where expander 221 is a balloon, some embodiments include controlling the inflation pressure of the expander 221. The expander 221 can comprise one or more pressure sensors and a system to communicate the internal pressure to the practitioner. The device can include a pressure control system based on sensor feedback that prevents the balloon from underinflation or overinflation.

The braided assembly 219 may incorporate features that facilitate removal of the thrombus. In some embodiments, the wires 217 of braid 209 can be adapted to shave or scrape off pieces of the thrombus as the braided assembly 219 is moved relative to the thrombus. For example, the wires 217 can be flattened to help macerate the thrombus. In some examples, the retrieval device 271 can be twisted around its longitudinal axis in order to rotate the wires 217 against the thrombus, thereby assisting with shaving, scraping, or macerating of the thrombus. In some examples, the wires 217 can be pushed back and forth against the sides of the thrombus to facilitate its removal. Some braided assemblies 219 include an oscillating ring 213 that scrapes, shaves, or macerates the thrombus as the braided assembly 219 is moved or rotated against the thrombus. For example, the flat outer surface of ring 213 is pushed against the thrombus upon expansion of braided assembly 219. When the retrieval device 271 is moved longitudinally, force against the thrombus is concentrated in apices 215 to provide a shaving or scraping effect. The shaving or scraping helps to dislodge the thrombus and bring pieces of the thrombus toward aspiration catheter 263. The methods can further include clearing a clog within the aspiration catheter 263 using the wires 217 or the oscillating ring 213.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various implementations with various modifications as are suited to the particular use contemplated.

What is claimed is:

1. A thrombectomy device comprising:
an aspiration catheter comprising a proximal end, a beveled distal end, and a circumferentially extending blocking element coupled to an outer surface of the aspiration catheter adjacent to the beveled distal end, the beveled distal end comprising undulations extending to the distal tip and positioned sporadically around a distal edge of the distal tip to create a scalloped profile;
a thrombus retrieval device extending through the aspiration catheter and exiting beyond the beveled distal end, the retrieval device comprising a proximal region, a distal region, and a first lumen extending therebetween;
an activation wire extending through the first lumen of the retrieval device; and
at least one braided assembly coupled to the distal region of the retrieval device and to the activation wire, the braided assembly comprising a circumferentially extending, oscillating ring encircling a braid;
wherein the oscillating ring comprises a plurality of apices; and
wherein the braided assembly is expandable to a range of expanded outer diameters by varying the level of tension in the activation wire.

2. An aspiration catheter comprising:
a proximal end;
a beveled distal end; and
a circumferentially extending blocking element coupled to an outer surface of the aspiration catheter adjacent to the beveled distal end, the beveled distal end comprising undulations extending to the distal tip and positioned sporadically around a distal edge of the distal tip to create a scalloped profile.

3. The aspiration catheter of claim 2, further comprising an expander positioned beneath a braid of a braided assembly, the expander configured to exert an outward expansion force upon the braid.

4. The aspiration catheter of claim 2, wherein an angle of the distal edge of the beveled distal end increases traveling proximally along the edge.

5. The aspiration catheter of claim 2, wherein the beveled distal end comprises a material distinct from a material of proximally situated portions of the aspiration catheter.

6. The aspiration catheter of claim 2, wherein, in an expanded state, the blocking element extends outward farther from a first side of the aspiration catheter than from a second side of the aspiration catheter.

7. The aspiration catheter of claim 2, wherein the blocking element is coupled to the outer surface of the aspiration catheter along a blocking element fixation line, and the blocking element fixation line is sloped to approximate an angle of an edge of the beveled distal end.

8. The aspiration catheter of claim 7, wherein the blocking element fixation line is a distance of from 0 millimeters to 10 millimeters distal to the edge of the beveled distal end.

9. A thrombus retrieval device comprising:
a proximal region, a distal region, and a first lumen extending therebetween;
an activation wire extending through the first lumen of the retrieval device; and
at least one braided assembly coupled to the distal region of the retrieval device and to the activation wire, the braided assembly comprising first and second circumferentially extending, oscillating rings encircling a braid, the first oscillating ring circumferentially rotated as compared to the second oscillating ring such that each apex of a set of apices on the first oscillating ring occurs at a different circumferential location about the braid than a corresponding apex of a set of apices on the second oscillating ring; and
wherein the braided assembly is expandable to a range of expanded outer diameters by varying the level of tension in the activation wire.

10. The thrombus retrieval device of claim 9, wherein the oscillating ring comprises flat surfaces.

11. The thrombus retrieval device of claim 9, wherein the braid comprises a plurality of flat wires.

12. The thrombus retrieval device of claim 9, wherein the braid comprises a mixture of flat wires and round wires.

13. The thrombus retrieval device of claim 9, wherein the braid has a shape memory of a collapsed configuration.

14. The thrombus retrieval device of claim 9, wherein the braided assembly further comprises a slidable collar, and the braid is coupled to the slidable collar and extends toward a fixed attachment point that anchors the braid to the retrieval device, and wherein the activation wire exits the first lumen of the retrieval device via an exit point located on the distal region to attach to the slidable collar.

15. The thrombus retrieval device of claim 14, wherein the slidable collar encircles the retrieval device.

16. The thrombus retrieval device of claim 9, wherein the retrieval device comprises a proximal reinforcement segment, a central hypotube with a lower rigidity than the proximal reinforcement segment, and a distal support tube with a lower rigidity than the central hypotube.

17. The thrombus retrieval device of claim 16, wherein the proximal reinforcement segment comprises a lubricious coating.

18. The thrombus retrieval device of claim 9, further comprising a handle coupled to a proximal end of the retrieval device, the handle configured to lock the braided assembly in a fixed outer diameter.

19. The thrombus retrieval device of claim 18, wherein the handle comprises a locking slider configured to permit or prevent longitudinal movement of the activation wire.

20. The thrombus retrieval device of claim 19, wherein the handle comprises a first set of teeth and the locking slider comprises a second set of teeth, the first set of teeth engaged with the second set of teeth when the locking slider is in a locked configuration, and the first set of teeth disengaged with the second set of teeth when the locking slider is in a slidable configuration.

* * * * *